United States Patent
Hogg et al.

(10) Patent No.: US 9,422,332 B2
(45) Date of Patent: Aug. 23, 2016

(54) AZAHETEROCYCLES AS BIR2 AND/OR BIR3 INHIBITORS

(71) Applicant: Hoffmann-La Roche Inc., Nutley, NJ (US)

(72) Inventors: Joan Heather Hogg, Los Altos Hills, CA (US); Kang Le, Green Brook, NJ (US); Yan Lou, Pleasanton, CA (US); Steven Gregory Mischke, Waltham, MA (US); Stacy Remiszewski, Washington Township, NJ (US)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 14/419,288

(22) PCT Filed: Aug. 6, 2013

(86) PCT No.: PCT/EP2013/066458
§ 371 (c)(1),
(2) Date: Feb. 3, 2015

(87) PCT Pub. No.: WO2014/026882
PCT Pub. Date: Feb. 20, 2014

(65) Prior Publication Data
US 2015/0210739 A1    Jul. 30, 2015

Related U.S. Application Data

(60) Provisional application No. 61/683,253, filed on Aug. 15, 2012.

(51) Int. Cl.
| | | |
|---|---|---|
| C07D 405/06 | (2006.01) | |
| C07D 409/12 | (2006.01) | |
| C07D 209/44 | (2006.01) | |
| C07K 5/083 | (2006.01) | |
| C07D 217/26 | (2006.01) | |
| C07D 401/12 | (2006.01) | |

(52) U.S. Cl.
CPC ............ *C07K 5/0806* (2013.01); *C07D 209/44* (2013.01); *C07D 217/26* (2013.01); *C07D 401/12* (2013.01); *C07D 405/06* (2013.01); *C07D 409/12* (2013.01)

(58) Field of Classification Search
CPC ............................ C07D 405/06; C07D 409/12
See application file for complete search history.

(56) References Cited

FOREIGN PATENT DOCUMENTS

| WO | 2006017295 | 2/2006 |
|---|---|---|
| WO | 2011059763 | 5/2011 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Chao, et al. Document No. 144:233382, retreived from CAPLUS. Entered in STN on Feb. 17, 2006.*
Maillard et al., "Exploiting differences in caspase-2 and -3 S2 subsites for selectivity: Structure-based design, solid-phase synthesis and in vitro activity of novel substrate-based caspase-2 inhibitors," Bioorganic & Medicinal Chemistry 19 (2011) 5833-5851.
The International Search Report and Written Opinion, issued on Nov. 28, 2013, in the corresponding PCT Patent Application No. PCT/EP2013/066458.
The English translation of the Chinese Office Action, issued on Dec. 30, 2015, in the corresponding Chinese Application No. 201380035682.3.

* cited by examiner

*Primary Examiner* — Shawquia Jackson

(57) ABSTRACT

Disclosed are compounds of Formula (I) or pharmaceutically acceptable salts thereof, wherein $R^1$, $R^2$, $R^3$, m, n and q are described in this application, and methods of using said compounds in the treatment of cancer.

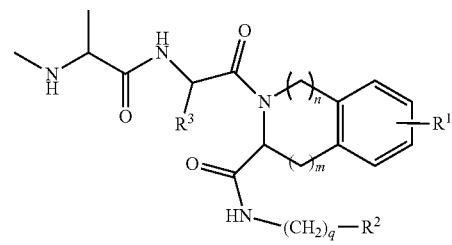

23 Claims, No Drawings

SEQUENCE LISTING

<160> NUMBER OF SEQ ID NOS: 3

<210> SEQ ID NO 1
<211> LENGTH: 10
<212> TYPE: PRT
<213> ORGANISM: Artificial Sequence
<220> FEATURE:
<223> OTHER INFORMATION: TR-FRET peptide

<400> SEQUENCE: 1

Ala Val Pro Ile Ala Gln Lys Ser Glu Lys
1               5                   10

<210> SEQ ID NO 2
<211> LENGTH: 125
<212> TYPE: PRT
<213> ORGANISM: Artificial Sequence
<220> FEATURE:
<223> OTHER INFORMATION: TR-FRET peptide

<400> SEQUENCE: 2

Met Arg His His His His His His Arg Asp His Phe Ala Leu Asp Arg
1               5                   10                  15

Pro Ser Glu Thr His Ala Asp Tyr Leu Leu Arg Thr Gly Gln Val Val
                20                  25                  30

Asp Ile Ser Asp Thr Ile Tyr Pro Arg Asn Pro Ala Met Tyr Ser Glu
            35                  40                  45

Glu Ala Arg Leu Lys Ser Phe Gln Asn Trp Pro Asp Tyr Ala His Leu
        50                  55                  60

Thr Pro Arg Glu Leu Ala Ser Ala Gly Leu Tyr Tyr Thr Gly Ile Gly
65                  70                  75                  80

Asp Gln Val Gln Cys Phe Ala Cys Gly Gly Lys Leu Lys Asn Trp Glu
                85                  90                  95

Pro Gly Asp Arg Ala Trp Ser Glu His Arg Arg His Phe Pro Asn Cys
            100                 105                 110

Phe Phe Val Leu Gly Arg Asn Leu Asn Ile Arg Ser Glu
        115                 120                 125

```
<210> SEQ ID NO 3
<211> LENGTH: 125
<212> TYPE: PRT
<213> ORGANISM: Artificial Sequence
<220> FEATURE:
<223> OTHER INFORMATION: TR-FRET peptide

<400> SEQUENCE: 3

Met Arg His His His His His His Arg Ser Asp Ala Val Ser Ser Asp
1               5                   10                  15

Arg Asn Phe Pro Asn Ser Thr Asn Leu Pro Arg Asn Pro Ser Met Ala
            20                  25                  30

Asp Tyr Glu Ala Arg Ile Phe Thr Phe Gly Thr Trp Ile Tyr Ser Val
            35                  40                  45

Asn Lys Glu Gln Leu Ala Arg Ala Gly Phe Tyr Ala Leu Gly Glu Gly
        50                  55                  60

Asp Lys Val Lys Cys Phe His Cys Gly Gly Gly Leu Thr Asp Trp Lys
65                  70                  75                  80

Pro Ser Glu Asp Pro Trp Glu Gln His Ala Lys Trp Tyr Pro Gly Cys
                85                  90                  95

Lys Tyr Leu Leu Glu Gln Lys Gly Gln Glu Tyr Ile Asn Asn Ile His
            100                 105                 110

Leu Thr His Ser Leu Glu Glu Cys Leu Val Arg Thr Thr
            115                 120                 125
```

AZAHETEROCYCLES AS BIR2 AND/OR BIR3 INHIBITORS

CROSS-REFERENCE TO RELATED APPLICATIONS

This application is a National Stage Application of PCT/EP2013/066458 filed Aug. 6, 2013, which claims priority from U.S. Provisional Patent Application No. 61/683,253, filed on Aug. 15, 2012. The priority of both said PCT and U.S. Provisional Patent Application are claimed. Each of prior mentioned applications is hereby incorporated by reference herein in its entirety.

FIELD OF THE INVENTION

The present invention relates to substituted isoindolines and tetrahydro-isoquinolines which act as inhibitors of SMAC protein binding to Inhibitor of Apoptosis Proteins (IAPs), and/or inhibitors of activated caspase protein binding to IAPs. These molecules are useful in the amelioration, treatment or control of cancer, especially solid tumors.

These compounds bind to the BIR2 and/or BIR3 regions of IAP proteins, including XIAP and cIAP, resulting in activation or reactivation of the caspase cascade and, as such, are useful for the treatment of proliferative diseases, including cancer.

BACKGROUND OF THE INVENTION

Cancer is a disease of uncontrolled cell growth causing local expansion of a tumor and, potentially, distant metastases. One mechanism by which cancer cells grow is by avoidance of apoptosis, or programmed cell death. Alterations in apoptotic pathways have been linked to cancer cells being resistant to standard treatments, e.g., chemotherapeutics or radiation, and to the incidence and progression of cancer. See, e.g., E. Dean et al., "X-linked inhibitor of apoptosis protein as a therapeutic target," Expert Opin. Ther. Targets (2007) 11(11):1459-1471

The two basic pathways for apoptotic cell death are the intrinsic pathway and the extrinsic pathway. The intrinsic apoptotic pathway can be initiated by various mechanisms including cellular stress and drug-induced DNA damage. The extrinsic pathway can be initiated by activation of the death receptors by a chemokine. Initiation of either pathway results in the activation of a family of proteases called caspases. Once activated, the caspases can act to cleave a variety of substrates creating a cascade of events that lead to the activation of the effector caspases 3 and 7 and eventual cell death. The IAP family of proteins can bind to and inhibit the activity of caspases thus inhibiting apoptosis. See, e.g., Dean, supra at 1460.

The IAPs can contain up to three copies of homologous structural domains called baculoviral IAP repeat (BIR) domains, BIR1, BIR2 and BIR3. The BIR3 domain of the prototypical IAPs, cIAP and XIAP, can bind to and inhibit activated caspase 9. The BIR2 domain, in contrast, binds to and inhibits caspases 3 and 7. The proapoptotic protein Smac (also known as DIABLO) can block the BIR2 and BIR3 domains of IAPs competing with activated caspases resulting in release of the activated caspases from the IAPs and completion of the apoptotic program. See, e.g., S. Wang, "Design of Small-Molecule Smac Mimetics as IAP Antagonists," Current Topics in Microbiology and Immunology 348, DOI 10.1007/82_2010_111, pp. 89-113.

Peptides and small molecules have been reported to bind to the BIR3 region of XIAP and cIAP, mimicking the action of Smac protein and releasing activated caspases. See, e.g., Dean, supra; and M. Gyrd-Hanse et al., "IAPs: From caspase inhibitors to modulators of NF-κB, inflammation and cancer," Nature Review/Cancer, August 2010, Vol 10:561-574.

SUMMARY OF THE INVENTION

One aspect of the present invention is a compound of Formula I

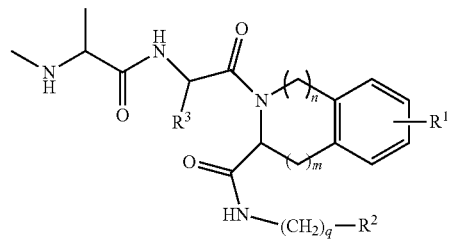

or pharmaceutically acceptable salts thereof, wherein $R^1$, $R^2$, $R^3$, m, n and q are described in this application.

The present invention also relates to pharmaceutical compositions comprising one or more compounds of the invention, or a pharmaceutically acceptable salt thereof, and a pharmaceutically acceptable carrier or excipient.

The present invention further relates to a method of ameliorating, controlling or treating cancer, including specifically solid tumors, for example lung, pancreatic, colon, breast, bone and prostate cancers in a mammal, specifically a human, comprising administering to said mammal a therapeutically effective amount of a compound according to the invention or a pharmaceutically acceptable salt thereof.

DETAILED DESCRIPTION OF THE INVENTION

Definitions

Unless otherwise defined, all technical and scientific terms used herein have the same meaning as commonly understood by one of ordinary skill in the art to which this invention belongs.

As used herein, the following terms shall have the following definitions.

"Alkyl" means a monovalent linear or branched saturated hydrocarbon of 1 to 12 carbon atoms. In particular embodiments, alkyl has 1 to 6 carbon atoms, and in more particular embodiments 1 to 4 carbon atoms. As used herein, "lower alkyl" denotes an alkyl group having from 1-6 carbon atoms ("$C_{1-6}$-alkyl"). Examples of alkyl include methyl, ethyl, propyl, isopropyl, butyl (also known as n-butyl), iso-butyl, sec-butyl, tert-butyl, pentyl, hexyl, and the like. The alkyl group can be optionally enriched in deuterium, e.g., —$CD_3$, —$CD_2CD_3$ and the like.

"Aryl" means a monovalent aromatic carbocyclic mono-, bi- or tricyclic ring system comprising 6 to 19 carbon ring atoms. Examples of aryl moieties include, but are not limited to, phenyl, naphthyl (or naphathelenyl), tolyl, xylyl, pyridinyl, quinolinyl, pyrimidinyl, imidazolyl, thiazolyl, anthracenyl, tetrazolyl, and fluorenyl. A particular aryl is phenyl.

"Cycloalkyl" means a substituted on unsubstituted stable monovalent saturated monocyclic, bicyclic or tricyclic system which consists of 3 to 10 ring carbon atoms. In particular embodiments cycloalkyl denotes a monovalent saturated monocyclic hydrocarbon group of 3 to 8 ring carbon atoms, more particular of 3 to 7 carbon atoms ("$C_{3-7}$-cycloalkyl"). Particular cycloalkyl groups are monocyclic. Examples for monocyclic cycloalkyl are cyclopropyl, cyclobutnyl, cyclopentyl, cyclohexyl or cycloheptyl. Bicyclic means consisting of two saturated carbocycles having one or more carbon atoms in common. Examples for bicyclic cycloalkyl are bicyclo[2.2.1]heptanyl, or bicyclo[2.2.2]octanyl. Tricyclic means consisting of three saturated carbocycles having two or more carbon atoms in common. Examples of tricyclic cycloalkyl include adamantane.

"Fused" when referring to two or more rings, e.g. aryl fused with cycloalkyl, means that the rings have at least two atoms in common. An example of aryl fused with cycloalkyl is tetrahydronaphthalenyl.

"Halogen" or "Halo" means at atom selected from F, Cl, Br or I. In particular embodiments Halogen means F and Cl.

"Heteroatom" means at atom selected from N, O or S.

"Heteroaryl" means a substituted or unsubstituted aromatic heterocyclic ring system containing up to two rings, at least one ring of which includes 1, 2, or 3 heteroatoms, the remaining ring atoms being carbon. Examples of heteroaryl groups include, but are not limited to, thienyl (or thiophenyl), furyl (or furanyl), indolyl, pyrrolyl, pyridinyl, pyrazinyl, oxazolyl, isoxazolyl, oxadiazolyl, thiazolyl, quinolinyl, isoquinolinyl, indazolyl, pyrimidinyl, imidazolyl, triazolyl, tetrazolyl, triazinyl, pyrazolyl, benzo[d]isoxazolyl, 2-oxo-2H-chromen-4-yl, benzo[d]isoxazolyl, benzo[b]thiophenyl, naphthyrydinyl and cinnolinyl.

In the case of a heteroaryl that is bicyclic it should be understood that one ring may be aryl while the other is heteroaryl and both may be independently substituted or unsubstituted.

"Heterocyclyl," "heterocycle" or "heterocyclic ring" means a substituted or unsubstituted monovalent saturated or partly unsaturated mono- or bicyclic ring, non-aromatic hydrocarbon system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, tetrahydrofuranyl, piperazinyl, morpholinyl, thiomorpholinyl, 1,1-dioxo-thiomorpholin-4-yl, azepanyl, diazepanyl, homopiperazinyl, or oxazepanyl. Examples of partly unsaturated heterocycloalkyl are dihydrofuryl, imidazolinyl, dihydro-oxazolyl, dihydro-oxadiazolyl, dihydro-triazolyl, tetrahydro-pyridinyl, tetrahydro-triazinyl or dihydropyranyl.

In the case of a heterocycle that is bicyclic it should be understood that one ring may be heterocycle while the other is cycloalkyl, and either or both may be independently substituted. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl.

"$IC_{50}$" refers to the concentration of a particular compound required to inhibit 50% of a specific measured activity. $IC_{50}$ can be measured, inter alia, as is described subsequently in Example 48.

"Oxo" or ("Oxy") means =O.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoroacetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (1995) at pgs. 456-457.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (1995) at pgs. 456-457.

"Substituted," as in substituted alkyl, aryl or heteroaryl means that the substitution (i.e. replacement of one hydrogen atom) can occur at one or more positions and, unless otherwise indicated, that the substituents at each substitution site are independently selected from the specified options. The term "optionally substituted" refers to the fact that one or more hydrogen atoms of a chemical group (with one or more hydrogen atoms) can be, but does not necessarily have to be, substituted with another substituent.

The definitions described herein apply irrespective of whether the terms in question appear alone or in combination. It is contemplated that the definitions described herein can be appended to form chemically-relevant combinations, such as e.g. "heterocycloalkylaryl", "haloalkylheteroaryl" or "arylalkylheterocycloalkyl". The last member of the combination is the radical which is binding to the rest of the molecule. The other members of the combination are attached to the binding radical in reversed order in respect of the literal sequence, e.g. the combination arylalkylheterocycloalkyl refers to a heterocycloalkyl-radical which is substituted by an alkyl which is substituted by an aryl.

As used in this application, if a formula or group appears to be missing a substituent, that is it appears the valence is not complete, it is presumed the missing substituent is an H.

In the structural formulae presented herein a broken bond (a) denotes that the substituent is below the plane of the paper and a wedged bond (b) denotes that the substituent is above the plane of the paper.

In one embodiment, the present invention relates to compounds of Formula I

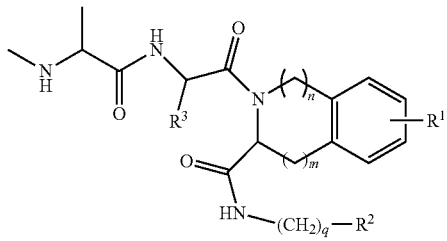

wherein:
$R^1$ is selected from H and halogen;
$R^2$ is selected from
aryl that optionally may be substituted with lower alkyl, $OR^4$, and halogen,
aryl that is fused with cycloalkyl, and
heteroaryl that optionally may be substituted with lower alkyl;
$R^3$ is selected from
lower alkyl that optionally may be substituted with $OR^4$ and aryl,
cycloalkyl,
heterocyclyl, and
aryl;
$R^4$ is selected from H and lower alkyl;
n is 1 or 2;
m is 0 or 1; and
q is 0, 1 or 2;
or a pharmaceutically acceptable salt thereof In one embodiment, the present invention relates to a compound of Formula I:

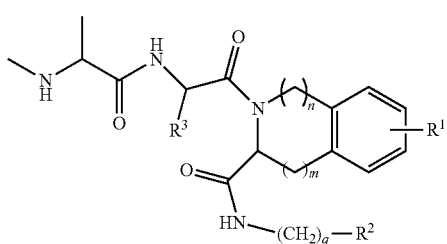

wherein:
$R^1$ is selected from H and halogen;
$R^2$ is selected from
aryl that optionally may be substituted with $C_{1-6}$-alkyl, $OR^4$, and halogen,
aryl that is fused with $C_{3-7}$-cycloalkyl, and
heteroaryl that optionally may be substituted with $C_{1-6}$-alkyl;

$R^3$ is selected from
$C_{1-6}$-alkyl that optionally may be substituted with $OR^4$ and aryl,
$C_{3-7}$-cycloalkyl,
heterocyclyl, and
aryl;
$R^4$ is selected from H and $C_{1-6}$-alkyl;
n is 1 or 2;
m is 0 or 1; and
q is 0, 1 or 2;
or a pharmaceutically acceptable salt of the foregoing compound.

In one embodiment, the present invention relates to a compound as described herein wherein $R^1$ is halogen, or a pharmaceutically acceptable salt thereof.

In one embodiment, the present invention relates to a compound as described herein wherein $R^1$ is H.

In one embodiment, the present invention relates to a compound as described herein wherein $R^2$ is aryl that optionally may be substituted with $OR^4$, halogen and $C_{1-6}$-alkyl, or a pharmaceutically acceptable salt thereof.

In one embodiment, the present invention relates to a compound as described herein wherein $R^2$ is phenyl or naphthalenyl, or a pharmaceutically acceptable salt thereof.

In one embodiment, the present invention relates to a compound as described herein wherein $R^2$ is heteroaryl that optionally may be substituted with $C_{1-6}$-alkyl, or a pharmaceutically acceptable salt thereof.

In one embodiment, the present invention relates to a compound as described herein wherein $R^2$ is selected from selected from quinolinyl, benzo[b]thiophenyl or indolyl.

In one embodiment, the present invention relates to a compound as described herein wherein $R^3$ is $C_{1-6}$-alkyl that optionally may be substituted with $OR^4$ and aryl, or a pharmaceutically acceptable salt thereof.

In one embodiment, the present invention relates to a compound as described herein wherein $R^3$ is $C_{1-6}$-alkyl substituted with phenyl, or a pharmaceutically acceptable salt thereof In one embodiment, the present invention relates to a compound as described herein wherein $R^3$ is $OR^4$ and $R^4$ is H, or a pharmaceutically acceptable salt thereof In one embodiment, the present invention relates to a compound as described herein wherein $R^3$ is $C_{3-7}$-cycloalkyl, or a pharmaceutically acceptable salt thereof.

In one embodiment, the present invention relates to a compound as described herein wherein $R^3$ is cyclohexyl or cyclopentyl, or a pharmaceutically acceptable salt thereof In one embodiment, the present invention relates to a compound as described herein wherein $R^3$ is aryl, or a pharmaceutically acceptable salt thereof.

In one embodiment, the present invention relates to a compound as described herein wherein $R^3$ is phenyl.

In one embodiment, the present invention relates to a compound as described herein wherein $R^3$ is heterocyclyl, or a pharmaceutically acceptable salt thereof.

In one embodiment, the present invention relates to a compound as described herein wherein $R^3$ is tetrahydropyran.

In one embodiment, the present invention relates to a compound as described herein wherein m is 0, n is 1, and q is 0, or a pharmaceutically acceptable salt thereof In one embodiment, the present invention relates to a compound as described herein wherein $R^1$ is H, $R^2$ is aryl, $R^3$ is $C_{1-6}$-alkyl, n is 1 and m and q are 0.

In one embodiment, the present invention relates to a compound as described herein wherein $R^3$ is $C_{1-6}$-alkyl, n is 1 and m is 0, said compound being selected from the group comprising:

(S)-2-[(S)-3-Methyl-2-((S)-2-methylamino-propionylamino)-butyryl]-2,3-dihydro-1H-isoindole-1-carboxylic acid (2,6-difluoro-phenyl)-amide hydrochloride;

((S)—N-(2,6-dichlorophenyl)-2-((S)-3-methyl-2-((S)-2-(methylamino)propanamido) butanoyl)isoindoline-1-carboxamide hydrochloride;

(S)—N-(2-chloro-6-fluorophenyl)-2-((S)-3-methyl-2-((S)-2-(methylamino) propanamido)butanoyl)isoindoline-1-carboxamide hydrochloride;

(S)—N-(benzo[b]thiophen-4-yl)-2-((S)-3-methyl-2-((S)-2-(methylamino)propanamido)butanoyl)isoindoline-1-carboxamide hydrochloride;

(S)—N-(2,6-difluorophenyl)-2-((2S,3S)-3-methyl-2-((S)-2-(methylamino) propanamido)pentanoyl)isoindoline-1-carboxamide hydrochloride;

(S)—N-(2,6-difluorophenyl)-2-((S)-3,3-dimethyl-2-((S)-2-(methylamino)propanamido)butanoyl)isoindoline-1-carboxamide hydrochloride;

2-((S)-3-methyl-2-((S)-2-(methylamino)propanamido)butanoyl)-N-phenylisoindoline-1-carboxamide hydrochloride;

N-(2-methoxyphenyl)-2-((S)-3-methyl-2-((S)-2-(methylamino)propanamido) butanoyl)isoindoline-1-carboxamide hydrochloride;

N-(2-methoxyphenyl)-2-((S)-3-methyl-2-((S)-2-(methylamino)propanamido) butanoyl)isoindoline-1-carboxamide hydrochloride;

N-benzyl-2-((S)-3-methyl-2-((S)-2-(methylamino)propanamido)butanoyl)isoindoline-1-carboxamide hydrochloride;

2-((S)-3-methyl-2-((S)-2-(methylamino)propanamido)butanoyl)-N-phenethylisoindoline-1-carboxamide hydrochloride;

(S)-2-((S)-3-methyl-2-((S)-2-(methylamino)propanamido)butanoyl)-N-(naphthalen-1-yl)isoindoline-1-carboxamide hydrochloride;

(R)-2-((S)-3-methyl-2-((S)-2-(methylamino)propanamido)butanoyl)-N-(naphthalen-1-yl)isoindoline-1-carboxamide hydrochloride;

(S)-2-((S)-3-methyl-2-((S)-2-(methylamino)propanamido)butanoyl)-N-(naphthalen-2-yl)isoindoline-1-carboxamide hydrochloride;

(S)—N-(2-fluorophenyl)-2-((S)-3-methyl-2-((S)-2-(methylamino)propanamido) butanoyl)isoindoline-1-carboxamide hydrochloride;

(S)—N-(2-chlorophenyl)-2-((S)-3-methyl-2-((S)-2-(methylamino)propanamido) butanoyl)isoindoline-1-carboxamide hydrochloride;

(S)-2-((S)-3-methyl-2-((S)-2-(methylamino)propanamido)butanoyl)-N-(5,6,7,8-tetrahydronaphthalen-1-yl)isoindoline-1-carboxamide hydrochloride;

(S)-2-((S)-3-methyl-2-((S)-2-(methylamino)propanamido)butanoyl)-N-(quinolin-8-yl)isoindoline-1-carboxamide hydrochloride;

N-(isoquinolin-1-yl)-2-((S)-3-methyl-2-((S)-2-(methylamino)propanamido) butanoyl)isoindoline-1-carboxamide hydrochloride;

(S)—N-(1-methyl-1H-indol-4-yl)-2-((S)-3-methyl-2-((S)-2-(methylamino)propanamido)butanoyl)isoindoline-1-carboxamide hydrochloride;

(S)—N-(2,6-difluorophenyl)-2-((2S,3S)-3-methoxy-2-((S)-2-(methylamino) propanamido)butanoyl)isoindoline-1-carboxamide hydrochloride;

(S)—N-(2,6-difluorophenyl)-2-((2S,3R)-3-hydroxy-2-((S)-2-(methylamino) propanamido)butanoyl)isoindoline-1-carboxamide hydrochloride;

(S)—N-(2,6-difluorophenyl)-2-((S)-4-methyl-2-((S)-2-(methylamino)propanamido)pentanoyl)isoindoline-1-carboxamide hydrochloride;

(S)—N-(2,6-difluorophenyl)-2-((2S,3S)-2-((S)-2-(methylamino)propanamido)-3-phenylbutanoyl)isoindoline-1-carboxamide hydrochloride; and (S)—N-(2-fluoro-6-methylphenyl)-2-((S)-3-methyl-2-((S)-2-(methylamino) propanamido)butanoyl)isoindoline-1-carboxamide hydrochloride;

or a pharmaceutically acceptable salt of any of the foregoing compounds.

In one embodiment, the present invention relates to a compound as described herein wherein $R^3$ is $C_{1-6}$-alkyl, n is 2 and m is 0, said compound being selected from the group comprising:

(S)-2-[(S)-3-Methyl-2-((S)-2-methylamino-propionylamino)-butyryl]-1,2,3,4-tetrahydro-isoquinoline-1-carboxylic acid (2-chloro-6-fluoro-phenyl)-amide hydrochloride;

6-Chloro-2-[(S)-3-methyl-2-((S)-2-methylamino-propionylamino)-butyryl]-1,2,3,4-tetrahydro-isoquinoline-1-carboxylic acid (2,6-difluoro-phenyl)-amide;

6-Fluoro-2-[(S)-3-methyl-2-((S)-2-methylamino-propionylamino)-butyryl]-1,2,3,4-tetrahydro-isoquinoline-1-carboxylic acid (2,6-difluoro-phenyl)-amide;

(S)—N-(2,6-difluorophenyl)-2-((2S,3S)-3-methyl-2-((S)-2-(methylamino) propanamido)pentanoyl)-1,2,3,4-tetrahydroisoquinoline-1-carboxamide hydrochloride;

(S)—N-(2,6-difluorophenyl)-2-((S)-3-methyl-2-((S)-2-(methylamino) propanamido)butanoyl)-1,2,3,4-tetrahydroisoquinoline-1-carboxamide hydrochloride;

(S)—N-(2,6-dichlorophenyl)-2-((S)-3-methyl-2-((S)-2-(methylamino)propanamido) butanoyl)-1,2,3,4-tetrahydroisoquinoline-1-carboxamide hydrochloride;

(S)—N-(2,6-difluorophenyl)-2-((S)-3,3-dimethyl-2-((S)-2-(methylamino)propanamido)butanoyl)-1,2,3,4-tetrahydroisoquinoline-1-carboxamide hydrochloride;

(S)—N-(2,6-difluorophenyl)-2-((2S,3R)-3-methoxy-2-((S)-2-(methylamino) propanamido)butanoyl)-1,2,3,4-tetrahydroisoquinoline-1-carboxamide hydrochloride;

N-(2,6-difluorophenyl)-7-fluoro-2-((S)-3-methyl-2-((S)-2-(methylamino) propanamido)butanoyl)-1,2,3,4-tetrahydroisoquinoline-1-carboxamide;

N-(2,6-difluorophenyl)-7-fluoro-2-((S)-3-methyl-2-((S)-2-(methylamino) propanamido)butanoyl)-1,2,3,4-tetrahydroisoquinoline-1-carboxamide;

N-(2,6-difluorophenyl)-6-fluoro-2-((S)-3-methyl-2-((S)-2-(methylamino) propanamido)butanoyl)-1,2,3,4-tetrahydroisoquinoline-1-carboxamide;

7-chloro-N-(2,6-difluorophenyl)-2-((S)-3-methyl-2-((S)-2-(methylamino) propanamido)butanoyl)-1,2,3,4-tetrahydroisoquinoline-1-carboxamide;

7-chloro-N-(2,6-difluorophenyl)-2-((S)-3-methyl-2-((S)-2-(methylamino) propanamido)butanoyl)-1,2,3,4-tetrahydroisoquinoline-1-carboxamide; and 6-chloro-N-(2,6-difluorophenyl)-2-((S)-3-methyl-2-((S)-2-(methylamino) propanamido)butanoyl)-1,2,3,4-tetrahydroisoquinoline-1-carboxamide;

or a pharmaceutically acceptable salt of any of the foregoing compounds.

In one embodiment, the present invention relates to a compound as described herein wherein $R^3$ is $C_{1-6}$-alkyl, n is 1 and m is 1, said compound being (S)—N-(2,6-difluorophenyl)-2-((S)-3-methyl-2-((S)-2-(methylamino)propanamido) butanoyl)-1,2,3,4-tetrahydroisoquinoline-3-carboxamide;
or a pharmaceutically acceptable salt thereof In one embodiment, the present invention relates to a compound as described herein wherein $R^3$ is $C_{3-7}$-cycloalkyl and n is 1, said compound being selected from the group comprising:
(S)-2-[(S)-2-Cyclohexyl-2-((S)-2-methylamino-propionylamino)-acetyl]-2,3-dihydro-1H-isoindole-1-carboxylic acid (2,6-difluoro-phenyl)-amide hydrochloride; and
(S)-2-((S)-2-cyclopentyl-2-((S)-2-(methylamino)propanamido)acetyl)-N-(2,6-difluorophenyl)isoindoline-1-carboxamide hydrochloride;
or a pharmaceutically acceptable salt of either of the foregoing compounds.

In one embodiment, the present invention relates to a compound as described herein wherein $R^3$ is $C_{3-7}$-cycloalkyl and n is 2, said compound being selected from the group comprising:
(S)-2-[(S)-2-Cyclohexyl-2-((S)-2-methylamino-propionylamino)-acetyl]-1,2,3,4-tetrahydro-isoquinoline-1-carboxylic acid (2,6-difluoro-phenyl)-amide hydrochloride; and
(S)-2-((S)-2-cyclopentyl-2-((S)-2-(methylamino)propanamido)acetyl)-N-(2,6-difluorophenyl)-1,2,3,4-tetrahydroisoquinoline-1-carboxamide hydrochloride;
or a pharmaceutically acceptable salt of either of the foregoing compounds.

In one embodiment, the present invention relates to a compound as described herein wherein $R^3$ is heterocyclyl, said compound being selected from the group comprising:
(S)—N-(2,6-difluorophenyl)-2-((S)-2-((S)-2-(methylamino)propanamido)-2-(tetrahydro-2H-pyran-4-yl)acetyl)isoindoline-1-carboxamide hydrochloride; and
(S)—N-(2,6-difluorophenyl)-2-((S)-2-((S)-2-(methylamino)propanamido)-2-(tetrahydro-2H-pyran-4-yl)acetyl)-1,2,3,4-tetrahydroisoquinoline-1-carboxamide hydrochloride;
or a pharmaceutically acceptable salt of either of the foregoing compounds.

In one embodiment, the present invention relates to a compound as described herein wherein $R^3$ is aryl, said compound being
(S)—N-(2,6-difluorophenyl)-2-((S)-2-((S)-2-(methylamino)propanamido)-2-phenylacetyl)isoindoline-1-carboxamide hydrochloride;
or a pharmaceutically acceptable salt of the foregoing compound.

In one embodiment, the present invention relates to a compound as described herein selected from the group comprising:
(S)-2-[(S)-3-Methyl-2-((S)-2-methylamino-propionylamino)-butyryl]-2,3-dihydro-1H-isoindole-1-carboxylic acid (2,6-difluoro-phenyl)-amide hydrochloride;
((S)-2-[(S)-2-Cyclohexyl-2-((S)-2-methylamino-propionylamino)-acetyl]-2,3-dihydro-1H-isoindole-1-carboxylic acid (2,6-difluoro-phenyl)-amide hydrochloride;
(S)—N-(2,6-difluorophenyl)-2-((S)-3-methyl-2-((S)-2-(methylamino) propanamido)butanoyl)isoindoline-1-carboxamide hydrochloride;
(S)-2-[(S)-3-Methyl-2-((S)-2-methylamino-propionylamino)-butyryl]-1,2,3,4-tetrahydro-isoquinoline-1-carboxylic acid (2-chloro-6-fluoro-phenyl)-amide hydrochloride;
6-Chloro-2-[(S)-3-methyl-2-((S)-2-methylamino-propionylamino)-butyryl]-1,2,3,4-tetrahydro-isoquinoline-1-carboxylic acid (2,6-difluoro-phenyl)-amide;
6-Fluoro-2-[(S)-3-methyl-2-((S)-2-methylamino-propionylamino)-butyryl]-1,2,3,4-tetrahydro-isoquinoline-1-carboxylic acid (2,6-difluoro-phenyl)-amide;
(S)—N-(2,6-dichlorophenyl)-2-((S)-3-methyl-2-((S)-2-(methylamino)propanamido) butanoyl)isoindoline-1-carboxamide hydrochloride;
(S)—N-(2-chloro-6-fluorophenyl)-2-((S)-3-methyl-2-((S)-2-(methylamino) propanamido)butanoyl)isoindoline-1-carboxamide hydrochloride;
(S)—N-(benzo[b]thiophen-4-yl)-2-((S)-3-methyl-2-((S)-2-(methylamino) propanamido)butanoyl)isoindoline-1-carboxamide hydrochloride;
(S)—N-(2,6-difluorophenyl)-2-((2S,3S)-3-methyl-2-((S)-2-(methylamino) propanamido)pentanoyl)isoindoline-1-carboxamide hydrochloride;
(S)—N-(2,6-difluorophenyl)-2-((S)-3,3-dimethyl-2-((S)-2-(methylamino) propanamido)butanoyl)isoindoline-1-carboxamide hydrochloride;
(S)—N-(2,6-difluorophenyl)-2-((S)-2-((S)-2-(methylamino) propanamido)-2-(tetrahydro-2H-pyran-4-yl)acetyl)isoindoline-1-carboxamide hydrochloride;
(S)-2-((S)-2-cyclopentyl-2-((S)-2-(methylamino)propanamido)acetyl)-N-(2,6-difluorophenyl)isoindoline-1-carboxamide hydrochloride;
(S)—N-(2,6-difluorophenyl)-2-((S)-2-((S)-2-(methylamino) propanamido)-2-(tetrahydro-2H-pyran-4-yl)acetyl)-1,2,3,4-tetrahydroisoquinoline-1-carboxamide hydrochloride;
(S)—N-(2,6-difluorophenyl)-2-((2S,3S)-3-methyl-2-((S)-2-(methylamino) propanamido)pentanoyl)-1,2,3,4-tetrahydroisoquinoline-1-carboxamide hydrochloride; and
N-(2,6-difluorophenyl)-7-fluoro-2-((S)-3-methyl-2-((S)-2-(methylamino) propanamido)butanoyl)-1,2,3,4-tetrahydroisoquinoline-1-carboxamide;

or a pharmaceutically acceptable salt of each of the foregoing compounds.

In one embodiment, the present invention relates to a pharmaceutical composition comprising any of the compounds as described herein, or a pharmaceutically acceptable salt thereof, as an active ingredient together with a pharmaceutically acceptable carrier or excipient.

In one embodiment, the present invention relates to a compound as described herein for use as a therapeutically active substance.

In one embodiment, the present invention relates to the use of a compound as described herein, or a pharmaceutically acceptable salt thereof, for the manufacture of a medicament for the therapeutic and/or prophylactic treatment of cancer.

In one embodiment, the present invention relates to the use of a compound as described herein, or a pharmaceutically acceptable salt thereof, for the therapeutic and/or prophylactic treatment of cancer.

In one embodiment, the present invention relates to a method of treating or ameliorating cancer comprising administering to a subject in need of such treatment a therapeutically effective amount of a compound as described herein.

In one embodiment, the present invention relates to compounds of Formula I

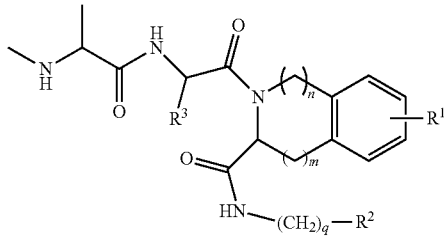

wherein:
R¹ is selected from H, Cl and F;
R² is selected from
phenyl,
phenyl that is substituted once ore twice by a substituent selected from with F, Cl, —CH₃ and —OCH₃,
naphthyl,
5,6,7,8-tetrahydronaphthyl,
benzo[b]thiophenyl,
quinolinyl,
isoquinolinyl, and
indolyl that optionally may be substituted with —CH₃;
R³ is selected from
isopropyl,
tert-butyl,
CH₃—CH₂—C(H,CH₃)—,
CH(CH₃)₂—CH₂—,
CH₃—CH₂—C(H₂OCH₃)—,
CH₃—C(H₂OH)—,
CH₃—C(H₂OCH₃)—
phenyl,
phenyl-C(H,CH₃)—,
tetrahydro-2H-pyranyl,
cyclopentyl, and
cyclohexyl;
R⁴ is selected from H and lower alkyl;
n is 1 or 2;
m is 0 or 1; and
q is 0, 1 or 2;
or a pharmaceutically acceptable salt thereof In one embodiment, the present invention relates to compounds of Formula I

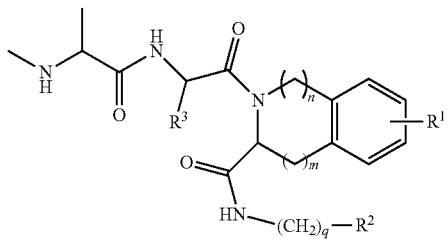

wherein:
R¹ is H;
R² is selected from
phenyl,
phenyl that is substituted once ore twice by a substituent selected from with F, Cl, —CH₃ and —OCH₃, and
naphthyl,
R³ is selected from
isopropyl,
tert-butyl,
CH₃—CH₂—C(H,CH₃)—,
CH(CH₃)₂—CH₂—,
CH₃—CH₂—C(H₂OCH₃)—,
CH₃—C(H₂OH)—, and
CH₃—C(H₂OCH₃)—
R⁴ is selected from H and lower alkyl;
n is 1;
m is 0; and
q is 0;
or a pharmaceutically acceptable salt thereof One embodiment of the invention relates to compounds of Formula I where R¹ is halogen, or a pharmaceutically acceptable salt thereof. In a particular embodiment, R¹ is F or Cl.

Another embodiment of the invention relates to compounds of Formula I where R¹ is H, or a pharmaceutically acceptable salt thereof Another embodiment of the invention relates to compounds of Formula I where R² is aryl that optionally may be substituted with OR⁴, halogen and lower alkyl, or a pharmaceutically acceptable salt thereof. In a particular embodiment R² is phenyl or naphthalenyl, each of which optionally may be substituted as defined above.

Another embodiment of the invention relates to compounds of Formula I where R² is heteroaryl that optionally may be substituted with lower alkyl, or a pharmaceutically acceptable salt thereof. In a particular embodiment R² is selected from quinolinyl, benzo[b]thiophenyl or indolyl.

Another embodiment of the invention relates to compounds of Formula I where R³ lower alkyl that optionally may be substituted with OR⁴ and aryl, or a pharmaceutically acceptable salt thereof. In a particular embodiment R³ is lower alkyl substituted with phenyl. In another embodiment R⁴ is H.

Another embodiment of the invention relates to compounds of Formula I where R³ is cycloalkyl, or a pharmaceutically acceptable salt thereof. In a particular embodiment R³ is cyclohexyl or cyclopentyl.

Another embodiment of the invention relates to compounds of Formula I where R³ is aryl, or a pharmaceutically acceptable salt thereof. In a particular embodiment R³ is phenyl.

Another embodiment of the invention relates to compounds of Formula I where R³ is heterocyclyl, or a pharmaceutically acceptable salt thereof. In a particular embodiment R³ is tetrahydropyran.

Another embodiment of the invention relates to compounds of Formula I where m is 0, or a pharmaceutically acceptable salt thereof.

Another embodiment of the invention relates to compounds of Formula I where n is 1, or a pharmaceutically acceptable salt thereof.

Another embodiment of the invention relates to compounds of Formula I where n is 2, or a pharmaceutically acceptable salt thereof.

Another embodiment of the invention relates to compounds of Formula I where q is 0, or a pharmaceutically acceptable salt thereof.

Another embodiment of the invention relates to compounds of Formula I where R¹ is H, R² is aryl, R³ is lower alkyl, n is 1 and m and q are 0.

Compounds according to the invention wherein R³ is alkyl that optionally may be substituted as defined above, n is 1, and m is 0 include:

(S)-2-[(S)-3-Methyl-2-((S)-2-methylamino-propionylamino)-butyryl]-2,3-dihydro-1H-isoindole-1-carboxylic acid (2,6-difluoro-phenyl)-amide hydrochloride (Example 1);

((S)—N-(2,6-dichlorophenyl)-2-((S)-3-methyl-2-((S)-2-(methylamino)propanamido) butanoyl)isoindoline-1-carboxamide hydrochloride (Example 7);

(S)—N-(2-chloro-6-fluorophenyl)-2-((S)-3-methyl-2-((S)-2-(methylamino) propanamido)butanoyl)isoindoline-1-carboxamide hydrochloride (Example 8);

(S)—N-(benzo[b]thiophen-4-yl)-2-((S)-3-methyl-2-((S)-2-(methylamino) propanamido)butanoyl)isoindoline-1-carboxamide hydrochloride (Example 9);

(S)—N-(2,6-difluorophenyl)-2-((2S,3S)-3-methyl-2-((S)-2-(methylamino) propanamido)pentanoyl)isoindoline-1-carboxamide hydrochloride (Example 10);

(S)—N-(2,6-difluorophenyl)-2-((S)-3,3-dimethyl-2-((S)-2-(methylamino) propanamido)butanoyl)isoindoline-1-carboxamide hydrochloride (Example 11);

2-((S)-3-methyl-2-((S)-2-(methylamino)propanamido)butanoyl)-N-phenylisoindoline-1-carboxamide hydrochloride (Example 16);

N-(2-methoxyphenyl)-2-((S)-3-methyl-2-((S)-2-(methylamino)propanamido) butanoyl)isoindoline-1-carboxamide hydrochloride (Example 17);

N-(2-methoxyphenyl)-2-((S)-3-methyl-2-((S)-2-(methylamino)propanamido) butanoyl)isoindoline-1-carboxamide hydrochloride (Example 18);

N-benzyl-2-((S)-3-methyl-2-((S)-2-(methylamino) propanamido)butanoyl)isoindoline-1-carboxamide hydrochloride (Example 19);

2-((S)-3-methyl-2-((S)-2-(methylamino)propanamido)butanoyl)-N-phenethylisoindoline-1-carboxamide hydrochloride (Example 20);

(S)-2-((S)-3-methyl-2-((S)-2-(methylamino)propanamido)butanoyl)-N-(naphthalen-1-yl)isoindoline-1-carboxamide hydrochloride (Example 21);

(R)-2-((S)-3-methyl-2-((S)-2-(methylamino)propanamido)butanoyl)-N-(naphthalen-1-yl)isoindoline-1-carboxamide hydrochloride (Example 22);

(S)-2-((S)-3-methyl-2-((S)-2-(methylamino)propanamido)butanoyl)-N-(naphthalen-2-yl)isoindoline-1-carboxamide hydrochloride (Example 23);

(S)—N-(2-fluorophenyl)-2-((S)-3-methyl-2-((S)-2-(methylamino)propanamido) butanoyl)isoindoline-1-carboxamide hydrochloride (Example 24);

(S)—N-(2-chlorophenyl)-2-((S)-3-methyl-2-((S)-2-(methylamino)propanamido) butanoyl)isoindoline-1-carboxamide hydrochloride (Example 26);

(S)-2-((S)-3-methyl-2-((S)-2-(methylamino)propanamido)butanoyl)-N-(5,6,7,8-tetrahydronaphthalen-1-yl)isoindoline-1-carboxamide hydrochloride (Example 27);

(S)-2-((S)-3-methyl-2-((S)-2-(methylamino)propanamido)butanoyl)-N-(quinolin-8-yl)isoindoline-1-carboxamide hydrochloride (Example 28);

N-(isoquinolin-1-yl)-2-((S)-3-methyl-2-((S)-2-(methylamino)propanamido) butanoyl)isoindoline-1-carboxamide hydrochloride (Example 29);

(S)—N-(1-methyl-1H-indol-4-yl)-2-((S)-3-methyl-2-((S)-2-(methylamino) propanamido)butanoyl)isoindoline-1-carboxamide hydrochloride (Example 30);

(S)—N-(2,6-difluorophenyl)-2-((2S,3S)-3-methoxy-2-((S)-2-(methylamino) propanamido)butanoyl)isoindoline-1-carboxamide hydrochloride (Example 32);

(S)—N-(2,6-difluorophenyl)-2-((2S,3R)-3-hydroxy-2-((S)-2-(methylamino) propanamido)butanoyl)isoindoline-1-carboxamide hydrochloride (Example 33);

(S)—N-(2,6-difluorophenyl)-2-((S)-4-methyl-2-((S)-2-(methylamino)propanamido)pentanoyl)isoindoline-1-carboxamide hydrochloride (Example 35);

(S)—N-(2,6-difluorophenyl)-2-((2S,3S)-2-((S)-2-(methylamino)propanamido)-3-phenylbutanoyl)isoindoline-1-carboxamide hydrochloride (Example 40); and (S)—N-(2-fluoro-6-methylphenyl)-2-((S)-3-methyl-2-((S)-2-(methylamino) propanamido)butanoyl)isoindoline-1-carboxamide hydrochloride (Example 47);

or a pharmaceutically acceptable salt of any of the foregoing compounds.

Compounds according to the invention wherein $R^3$ is alkyl that optionally may be substituted as defined above, n is 2 and m is 0 include:

(S)-2-[(S)-3-Methyl-2-((S)-2-methylamino-propionylamino)-butyryl]-1,2,3,4-tetrahydro-isoquinoline-1-carboxylic acid (2-chloro-6-fluoro-phenyl)-amide hydrochloride (Example 4);

6-Chloro-2-[(S)-3-methyl-2-((S)-2-methylamino-propionylamino)-butyryl]-1,2,3,4-tetrahydro-isoquinoline-1-carboxylic acid (2,6-difluoro-phenyl)-amide (Example 5);

6-Fluoro-2-[(S)-3-methyl-2-((S)-2-methylamino-propionylamino)-butyryl]-1,2,3,4-tetrahydro-isoquinoline-1-carboxylic acid (2,6-difluoro-phenyl)-amide (Example 6);

(S)—N-(2,6-difluorophenyl)-2-((2S,3S)-3-methyl-2-((S)-2-(methylamino) propanamido)pentanoyl)-1,2,3,4-tetrahydroisoquinoline-1-carboxamide hydrochloride (Example 15);

(S)—N-(2,6-difluorophenyl)-2-((S)-3-methyl-2-((S)-2-(methylamino) propanamido)butanoyl)-1,2,3,4-tetrahydroisoquinoline-1-carboxamide hydrochloride (Example 25);

(S)—N-(2,6-dichlorophenyl)-2-((S)-3-methyl-2-((S)-2-(methylamino)propanamido) butanoyl)-1,2,3,4-tetrahydroisoquinoline-1-carboxamide hydrochloride (Example 36);

(S)—N-(2,6-difluorophenyl)-2-((S)-3,3-dimethyl-2-((S)-2-(methylamino)propanamido)butanoyl)-1,2,3,4-tetrahydroisoquinoline-1-carboxamide hydrochloride (Example 38);

(S)—N-(2,6-difluorophenyl)-2-((2S,3R)-3-methoxy-2-((S)-2-(methylamino) propanamido)butanoyl)-1,2,3,4-tetrahydroisoquinoline-1-carboxamide hydrochloride (Example 39);

N-(2,6-difluorophenyl)-7-fluoro-2-((S)-3-methyl-2-((S)-2-(methylamino) propanamido)butanoyl)-1,2,3,4-tetrahydroisoquinoline-1-carboxamide (Example 41);

N-(2,6-difluorophenyl)-7-fluoro-2-((S)-3-methyl-2-((S)-2-(methylamino) propanamido)butanoyl)-1,2,3,4-tetrahydroisoquinoline-1-carboxamide (Example 42);

N-(2,6-difluorophenyl)-6-fluoro-2-((S)-3-methyl-2-((S)-2-(methylamino) propanamido)butanoyl)-1,2,3,4-tetrahydroisoquinoline-1-carboxamide (Example 43);

7-chloro-N-(2,6-difluorophenyl)-2-((S)-3-methyl-2-((S)-2-(methylamino) propanamido)butanoyl)-1,2,3,4-tetrahydroisoquinoline-1-carboxamide (Example 44);

7-chloro-N-(2,6-difluorophenyl)-2-((S)-3-methyl-2-((S)-2-(methylamino) propanamido)butanoyl)-1,2,3,4-tetrahydroisoquinoline-1-carboxamide (Example 45); and 6-chloro-N-(2,6-difluorophenyl)-2-((S)-3-methyl-2-((S)-2-(methylamino) propanamido)butanoyl)-1,2,3,4-tetrahydroisoquinoline-1-carboxamide (Example 46);

or a pharmaceutically acceptable salt of any of the foregoing compounds.

Compounds according to the invention wherein $R^3$ is alkyl that optionally may be substituted as defined above, n is 1 and m is 1 include:

(S)-2-[(S)-3-Methyl-2-((S)-2-methylamino-propionylamino)-butyryl]-1,2,3,4-tetrahydro-isoquinoline-3-carboxylic acid (2,6-difluoro-phenyl)-amide (Example 31);
or a pharmaceutically acceptable salt thereof Compounds according to the invention wherein $R^3$ is cycloalkyl and n is 1 include:
(S)-2-[(S)-2-Cyclohexyl-2-((S)-2-methylamino-propionylamino)-acetyl]-2,3-dihydro-1H-isoindole-1-carboxylic acid (2,6-difluoro-phenyl)-amide hydrochloride (Example 2); and
(S)-2-((S)-2-cyclopentyl-2-((S)-2-(methylamino)propanamido)acetyl)-N-(2,6-difluorophenyl)isoindoline-1-carboxamide hydrochloride (Example 13);
or a pharmaceutically acceptable salt of either of the foregoing compounds.

Compounds according to the invention wherein $R^3$ is cycloalkyl and n is 2 include:
(S)-2-[(S)-2-Cyclohexyl-2-((S)-2-methylamino-propionylamino)-acetyl]-1,2,3,4-tetrahydro-isoquinoline-1-carboxylic acid (2,6-difluoro-phenyl)-amide hydrochloride (Example 3); and
(S)-2-((S)-2-cyclopentyl-2-((S)-2-(methylamino)propanamido)acetyl)-N-(2,6-difluorophenyl)-1,2,3,4-tetrahydroisoquinoline-1-carboxamide hydrochloride (Example 37);
or a pharmaceutically acceptable salt of either of the foregoing compounds.

Compounds according to the invention wherein $R^3$ is heterocyclyl and n is 1 include:
(S)—N-(2,6-difluorophenyl)-2-((S)-2-((S)-2-(methylamino)propanamido)-2-(tetrahydro-2H-pyran-4-yl)acetyl)isoindoline-1-carboxamide hydrochloride (Example 12);
or a pharmaceutically acceptable salt thereof Compounds according to the invention wherein $R^3$ is heterocyclyl and n is 2 include:
(S)—N-(2,6-difluorophenyl)-2-((S)-2-((S)-2-(methylamino)propanamido)-2-(tetrahydro-2H-pyran-4-yl)acetyl)-1,2,3,4-tetrahydroisoquinoline-1-carboxamide hydrochloride (Example 14);
or a pharmaceutically acceptable salt of the foregoing compound.

Compounds according to the invention wherein $R^3$ is aryl and n is 1 include:
(S)—N-(2,6-difluorophenyl)-2-((S)-2-((S)-2-(methylamino)propanamido)-2-phenylacetyl)isoindoline-1-carboxamide hydrochloride (Example 34);
or a pharmaceutically acceptable salt of the foregoing compound.

Another embodiment of the invention relates to the following compounds:
(S)-2-[(S)-3-Methyl-2-((S)-2-methylamino-propionylamino)-butyryl]-2,3-dihydro-1H-isoindole-1-carboxylic acid (2,6-difluoro-phenyl)-amide hydrochloride (Example 1);
((S)-2-[(S)-2-Cyclohexyl-2-((S)-2-methylamino-propionylamino)-acetyl]-2,3-dihydro-1H-isoindole-1-carboxylic acid (2,6-difluoro-phenyl)-amide hydrochloride (Example 2);
(S)-2-[(S)-2-Cyclohexyl-2-((S)-2-methylamino-propionylamino)-acetyl]-1,2,3,4-tetrahydro-isoquinoline-1-carboxylic acid (2,6-difluoro-phenyl)-amide hydrochloride (Example 3);
(S)-2-[(S)-3-Methyl-2-((S)-2-methylamino-propionylamino)-butyryl]-1,2,3,4-tetrahydro-isoquinoline-1-carboxylic acid (2-chloro-6-fluoro-phenyl)-amide hydrochloride (Example 4);
6-Chloro-2-[(S)-3-methyl-2-((S)-2-methylamino-propionylamino)-butyryl]-1,2,3,4-tetrahydro-isoquinoline-1-carboxylic acid (2,6-difluoro-phenyl)-amide (Example 5);
6-Fluoro-2-[(S)-3-methyl-2-((S)-2-methylamino-propionylamino)-butyryl]-1,2,3,4-tetrahydro-isoquinoline-1-carboxylic acid (2,6-difluoro-phenyl)-amide (Example 6);
(S)—N-(2,6-dichlorophenyl)-2-((S)-3-methyl-2-((S)-2-(methylamino)propanamido) butanoyl)isoindoline-1-carboxamide hydrochloride (Example 7);
(S)—N-(2-chloro-6-fluorophenyl)-2-((S)-3-methyl-2-((S)-2-(methylamino) propanamido)butanoyl)isoindoline-1-carboxamide hydrochloride (Example 8);
(S)—N-(benzo[b]thiophen-4-yl)-2-((S)-3-methyl-2-((S)-2-(methylamino) propanamido)butanoyl)isoindoline-1-carboxamide hydrochloride (Example 9);
(S)—N-(2,6-difluorophenyl)-2-((2S,3S)-3-methyl-2-((S)-2-(methylamino) propanamido)pentanoyl)isoindoline-1-carboxamide hydrochloride (Example 10);
(S)—N-(2,6-difluorophenyl)-2-((S)-3,3-dimethyl-2-((S)-2-(methylamino) propanamido)butanoyl)isoindoline-1-carboxamide hydrochloride (Example 11);
(S)—N-(2,6-difluorophenyl)-2-((S)-2-((S)-2-(methylamino) propanamido)-2-(tetrahydro-2H-pyran-4-yl)acetyl)isoindoline-1-carboxamide hydrochloride (Example 12);
(S)-2-((S)-2-cyclopentyl-2-((S)-2-(methylamino)propanamido)acetyl)-N-(2,6-difluorophenyl)isoindoline-1-carboxamide hydrochloride (Example 13);
(S)—N-(2,6-difluorophenyl)-2-((S)-2-((S)-2-(methylamino) propanamido)-2-(tetrahydro-2H-pyran-4-yl)acetyl)-1,2,3,4-tetrahydroisoquinoline-1-carboxamide hydrochloride (Example 14);
(S)—N-(2,6-difluorophenyl)-2-((2S,3S)-3-methyl-2-((S)-2-(methylamino) propanamido)pentanoyl)-1,2,3,4-tetrahydroisoquinoline-1-carboxamide hydrochloride (Example 15); and
N-(2,6-difluorophenyl)-7-fluoro-2-((S)-3-methyl-2-((S)-2-(methylamino) propanamido)butanoyl)-1,2,3,4-tetrahydroisoquinoline-1-carboxamide (Example 42);
or a pharmaceutically acceptable salt of any of the foregoing compounds.

The compounds of Formula I as well as their salts have at least one asymmetric carbon atom and therefore may be present as mixtures of different stereoisomers. The various isomers can be isolated by known separation methods, e.g., chromatography.

Compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in the formulas above.

Dosages

The compounds of the invention preferably bind to BIR domains of an IAP preventing the IAP from binding to other proteins. Examples of Bir binding proteins include, but are not limited to, caspase 3, caspase 7, caspase 9, Smac and the like. Examples of IAPs include, but are not limited to, XIAP, cIAP1, cIAP2 or NAIP. In one aspect, the compound of the invention bind to the BIR2 and/or BIR3 domains of XIAP, cIAP1 and/or cIAP2. In another aspect, the compounds of the invention bind to the BIR2 domain of XIAP, cIAP1 and/or cIAP2.

Compounds of the invention are useful for inducing apoptosis in cells or sensitizing cells to apoptotic signals, in particular cancer cells. Apoptotic signals can be induced in cancer cells by, e.g., radiation therapy or antineoplastic chemotherapy. Alternatively, apoptotic signals can be induced in cancer cells by activation of the death receptors by death receptor agonists. Death receptor agonists can be naturally occurring, e.g., tumor necrosis factor α, (TNF-α) or non-naturally occurring, e.g., a synthetic antibody such as a DR4 or DR5 antibody.

The compounds of the present invention are thus useful in the amelioration, control or treatment of cell proliferative disorders such as, in particular, oncological disorders. These compounds and formulations containing said compounds are anticipated to be useful in the treatment or control of blood cancers, such as, for example, acute myeloid leukemia, or solid tumors, such as, for example, breast, colon, lung and prostate tumors.

A "therapeutically effective amount" or "effective amount" of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as one or more bolus injections or as a continuous infusion.

Pharmaceutical preparations useful in the practice of the invention, i.e., comprising the compounds of the invention can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions). Moreover, administration can be effected topically (e.g. in the form of ointments, creams or oils).

Compositions/Formulations

In an alternative embodiment, the present invention includes pharmaceutical compositions comprising at least one compound of formula I, or a pharmaceutically acceptable salt thereof, and a pharmaceutically acceptable excipient and/or carrier.

These pharmaceutical compositions can be suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

The compounds of Formula I and their pharmaceutically acceptable salts and esters can be processed with pharmaceutically inert, inorganic or organic adjuvants for the production of tablets, coated tablets, dragées and hard gelatin capsules. Lactose, polyvinylpyrrolidone, hydroxypropylmethylcellulose, hydroxypropyl-cellulose, microcrystalline cellulose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc. Suitable adjuvants for the production of solutions and syrups are, for example, $H_2O$, polyols, saccharose, invert sugar, glucose, etc. Suitable adjuvants for injection solutions are, for example, $H_2O$, alcohols, polyols, glycerol, vegetable oils, etc. Suitable adjuvants for suppositories are, for example, natural or hardened oils, waxes, fats, semi-solid or liquid polyols, etc. Suitable adjuvants for topical preparations are glycerides, semi-synthetic and synthetic glycerides, hydrogenated oils, liquid waxes, liquid paraffins, liquid fatty alcohols, sterols, polyethylene glycols and cellulose derivatives.

Moreover, the pharmaceutical preparations can contain preservatives, solubilizers, viscosity-increasing substances, stabilizers, wetting agents, emulsifiers, sweeteners, colorants, flavors, salts for varying the osmotic pressure, buffers, masking agents or antioxidants. They can also contain other therapeutic substances.

The compounds in the present invention (compounds of general Formula I) can be prepared using the general reaction scheme set out in Scheme 1 below.

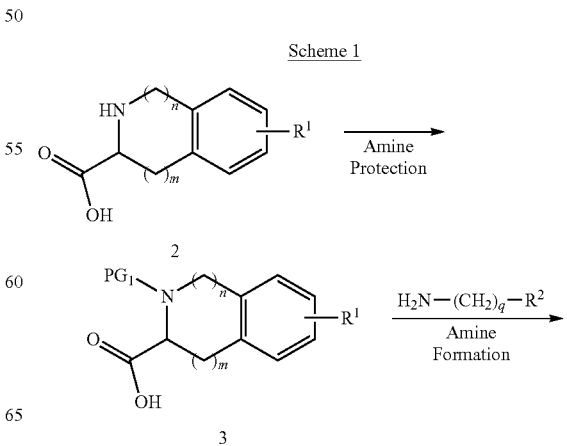

Scheme 1

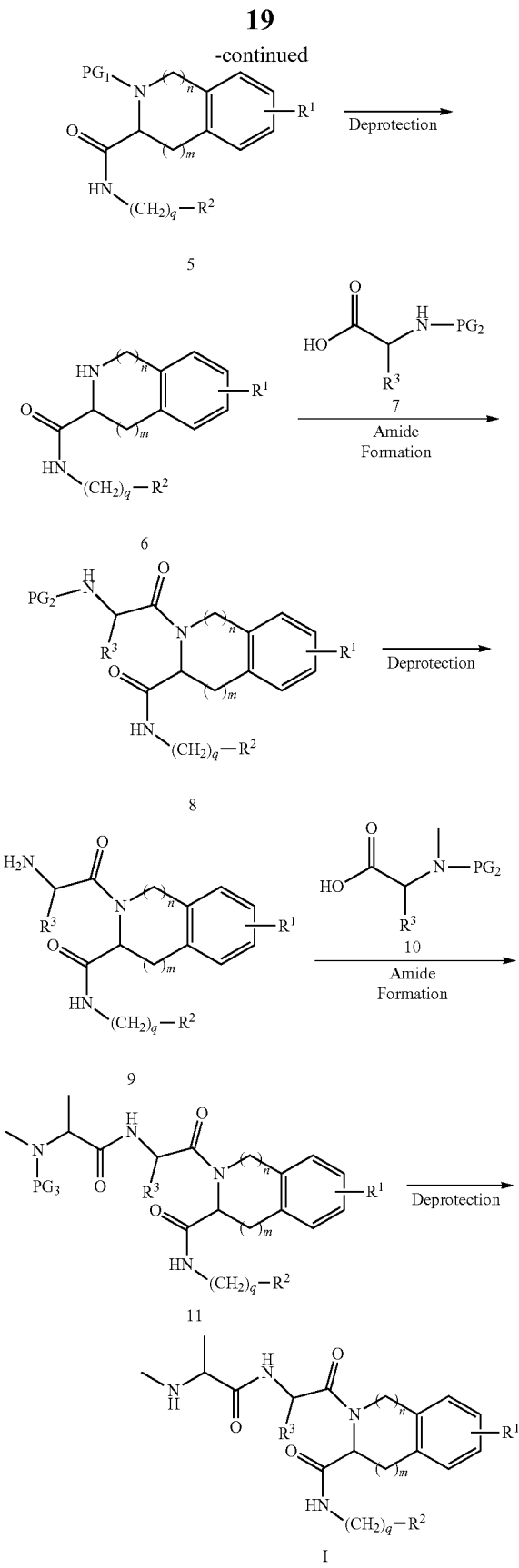

compounds of general formula 3. Compounds of general formula 3 can be reacted with a chlorinating agent, e.g., $POCl_3$, and an amine of general formula 4 to afford compounds of general formula 5. The protecting group PG1 in compounds of general formula 5 can be removed to afford compounds of general formula 6. Compounds of general formula 6 can treated with a suitably protected α-amino acid of general formula 7 under dehydrating conditions to provide compounds of general formula 8. The protecting group PG2 in compounds of general formula 8 can be removed to afford compounds of general formula 9. Compounds of general formula 9 can treated with a suitably protected α-amino acid of general formula 10 under dehydrating conditions to provide compounds of general formula 11. The protecting group PG3 in compounds of general formula 11 can be removed to afford compounds of general formula I.

Methods to perform the above described reactions and processes would be apparent to those of ordinary skill in the art based on the present disclosure, or can be deduced in analogy from the examples. Starting materials are commercially available or can be made by methods analogous to those described in the Examples below.

Crystal Forms

When the compounds of the invention are solids, it is understood by those skilled in the art that these compounds, and their salts, may exist in different crystal or polymorphic forms, all of which are intended to be within the scope of the present invention and specified formulas.

EXAMPLES

The compounds of the present invention may be synthesized according to known techniques. The following examples and references are provided to aid the understanding of the present invention. The examples are not intended, however, to limit the invention, the true scope of which is set forth in the appended claims. The names of the final products in the examples were generated using AutoNom 2000 Add-in v4.0 SP2 (function in ISIS Draw, Elsevier/MDL), or AutoNom 2000 TT v4.01.305 (Elsevier/MDL), or functions available in ChemDraw Pro Control 11.0.2 (CambridgeSoft Corp.), or Struct=Name feature of electronic notebooks.

Example 1

(S)-2-[(S)-3-Methyl-2-((S)-2-methylamino-propionylamino)-butyryl]-2,3-dihydro-1H-isoindole-1-carboxylic acid (2,6-difluoro-phenyl)-amide hydrochloride

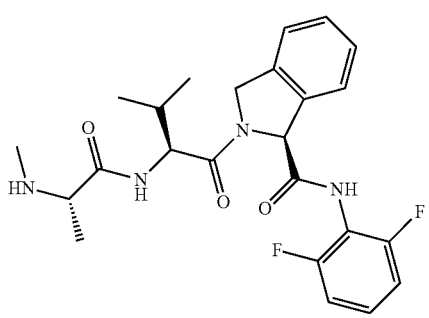 [SMILES: CN[C@@H](C)C(=O)N[C@H](C(=O)N1Cc2ccccc2[C@H]1C(=O)Nc1c(F)cccc1F)C(C)C]

Step 1: To a solution of 2-(tert-butoxycarbonyl)isoindoline-1-carboxylic acid (500 mg, 1.9 mmol, Eq: 1.00) and 2,6-difluoroaniline (294 mg, 2.28 mmol, Eq: 1.2) in pyridine (10 mL) at 0° C. was added POCl₃ (437 mg, 266 µL, 2.85 mmol, Eq: 1.5). The reaction was warmed to RT and stirred for 2 h. The mixture was evaporated and water was added and the resulting mixture was extracted with EtOAc. The combined organics were washed with water, brine, dried with MgSO₄ and concentrated in vacuo. The crude material was purified by flash chromatography to give 1-(2,6-difluoro-phenylcarbamoyl)-1,3-dihydro-isoindole-2-carboxylic acid tert-butyl ester (462 mg) as a light yellow foam.

Step 2: To a solution of 1-(2,6-difluoro-phenylcarbamoyl)-1,3-dihydro-isoindole-2-carboxylic acid tert-butyl ester (460 mg, 1.23 mmol, Eq: 1.00) in CH₂Cl₂ (6 mL) was added TFA (2 mL) dropwise. The reaction was stirred at RT for 1 h. The solvent was evaporated to afford 2,3-dihydro-1H-isoindole-1-carboxylic acid (2,6-difluoro-phenyl)-amide trifluoroacetate which was used without further purification.

Step 3: To a solution of 2,3-dihydro-1H-isoindole-1-carboxylic acid (2,6-difluoro-phenyl)-amide trifluoroacetate (477 mg, 1.23 mmol, Eq: 1.00), (S)-2-(tert-butoxycarbonylamino)-3-methylbutanoic acid (267 mg, 1.23 mmol, Eq: 1.00) and HATU (514 mg, 1.35 mmol, Eq: 1.1) in DMF (1.85 mL) at 0° C. was added DIEA
(476 mg, 644 µL, 3.69 mmol, Eq: 3). The reaction was stirred at RT for 1 h. Water was added and the mixture was extracted with EtOAc. The combined organics were washed with water, brine, dried with MgSO₄ and concentrated in vacuo. The crude material was purified by flash chromatography to afford two diastereomers. The less polar diastereomer was assigned as {(S)-1-[(S)-1-(2,6-difluoro-phenylcarbamoyl)-1,3-dihydro-isoindole-2-carbonyl]-2-methyl-propyl}-carbamic acid tert-butyl ester (220 mg) which was isolated as a white foam.

Step 4: To a solution of {(S)-1-[(S)-1-(2,6-difluoro-phenylcarbamoyl)-1,3-dihydro-isoindole-2-carbonyl]-2-methyl-propyl}-carbamic acid tert-butyl (210 mg, 443 µmol, Eq: 1.00) in CH₂Cl₂ (3 mL) was added TFA (1 mL) dropwise. The reaction was stirred at RT for 1 h. The solution was evaporated to afford (S)-2-((S)-2-amino-3-methyl-butyryl)-2,3-dihydro-1H-isoindole-1-carboxylic acid (2,6-difluoro-phenyl)-amide trifluoroacetate which was used without further purification.

Step 5: To a solution of (S)-2-((S)-2-amino-3-methyl-butyryl)-2,3-dihydro-1H-isoindole-1-carboxylic acid (2,6-difluoro-phenyl)-amide trifluoroacetate (216 mg, 443 µmol, Eq: 1.00), (S)-2-(tert-butoxycarbonyl-methyl-amino)-propionic acid (83.8 mg, 443 µmol, Eq: 1.00), HATU (185 mg, 487 µmol, Eq: 1.1) in DMF (500 µL) at 0° C. was added DIEA (172 mg, 232 µL, 1.33 mmol, Eq: 3). The reaction was stirred at RT for 1 h, diluted with water and extracted with EtOAc. The combined organics were washed with water, brine, dried with MgSO₄ and concentrated in vacuo. The crude material was purified by flash chromatography to give ((S)-1-{(S)-1-[(S)-1-(2,6-difluoro-phenylcarbamoyl)-1,3-dihydro-isoindole-2-carbonyl]-2-methyl-propylcarbamoyl}-ethyl)-methyl-carbamic acid tert-butyl ester ester (220 mg) as a white foam.

Step 6; A solution of acetyl chloride (552 mg, 500 µL, 7.03 mmol, Eq: 18.0) in MeOH (2 mL) was added to a vial containing ((S)-1-{(S)-1-[(S)-1-(2,6-difluoro-phenylcarbamoyl)-1,3-dihydro-isoindole-2-carbonyl]-2-methyl-propylcarbamoyl}-ethyl)-methyl-carbamic acid tert-butyl ester ester (218 mg, 390 µmol, Eq: 1.00). The mixture was stirred at RT for 1 h. The mixture was evaporated and the resulting solid was dissolved in MeCN (3 mL) and water (1 mL) and the solution lyophilized to give (S)-2-[(S)-3-methyl-2-((S)-2-methylamino-propionylamino)-butyryl]-2,3-dihydro-1H-isoindole-1-carboxylic acid (2,6-difluoro-phenyl)-amide hydrochloride (175 mg) as a white powder, m/z=459 (M+H).

Example 2

(S)-2-[(S)-2-Cyclohexyl-2-((S)-2-methylamino-propionylamino)-acetyl]-2,3-dihydro-1H-isoindole-1-carboxylic acid (2,6-difluoro-phenyl)-amide hydrochloride

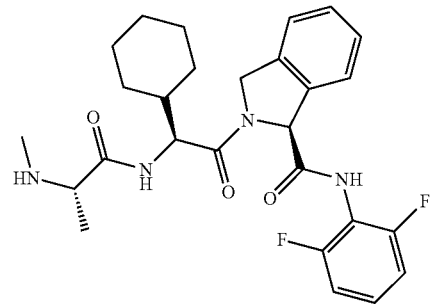 [SMILES: CN[C@@H](C)C(=O)N[C@H](C(=O)N1Cc2ccccc2[C@H]1C(=O)Nc1c(F)cccc1F)C1CCCCC1]

Step 1: To the solution of (S)-2-(tert-butoxycarbonyl)isoindoline-1-carboxylic acid (300 mg, 1.14 mmol, Eq: 1.00) and 2,6-difluoroaniline (177 mg, 1.37 mmol, Eq: 1.2) in pyridine (3.00 mL) at 0° C. was added POCl₃ (262 mg, 159 µL, 1.71 mmol, Eq: 1.5). The mixture was warmed to RT and stirred for 2 h. The mixture was evaporated, water was added and the mixture extracted with EtOAc. The combined organics were washed with water, brine, dried with MgSO₄ and concentrated in vacuo. The crude material was purified by flash chromatography to give (S)-1-(2,6-difluoro-phenylcarbamoyl)-1,3-dihydro-isoindole-2-carboxylic acid tert-butyl ester (298 mg) as a light yellow foam.

Step 2: To a solution of (S)-1-(2,6-difluoro-phenylcarbamoyl)-1,3-dihydro-isoindole-2-carboxylic acid tert-butyl ester in CH₂Cl₂ (3 mL) was added TFA (1 mL) dropwise. The reaction was stirred at RT for 1 h and the mixture evaporated to afford (S)-2,3-dihydro-1H-isoindole-1-carboxylic acid (2,6-difluoro-phenyl)-amide which was used without further purification.

Step 3: To a solution of (S)-2,3-dihydro-1H-isoindole-1-carboxylic acid (2,6-difluoro-phenyl)-amide (160 mg, 412 µmol, Eq: 1.00), (S)-2-(tert-butoxycarbonylamino)-2-cyclohexylacetic acid (106 mg, 412 µmol, Eq: 1.00) and HATU (172 mg, 453 µmol, Eq: 1.1) in DMF (500 µL) at 0° C. was added DIEA (160 mg, 216 µL, 1.24 mmol, Eq: 3). The reaction was stirred at RT for 1 h, diluted with water and extracted with EtOAc. The combined organics were washed with water, brine, dried with MgSO₄ and concentrated in vacuo. The crude material was purified by flash chromatography to give {(S)-1-cyclohexyl-2-[(S)-1-(2,6-difluoro-phenyl-carbamoyl)-1,3-dihydro-isoindol-2-yl]-2-oxo-ethyl}-carbamic acid tert-butyl ester (174 mg) as a white foam.

Step 4: To a solution of {(S)-1-cyclohexyl-2-[(S)-1-(2,6-difluoro-phenylcarbamoyl)-1,3-dihydro-isoindol-2-yl]-2-oxo-ethyl}-carbamic acid tert-butyl ester (174 mg, 339 µmol, Eq: 1.00) in CH₂Cl₂ (3 mL) was added TFA (1 mL) dropwise. The reaction was stirred at RT for 1 h. The mixture was evaporated to afford (S)-2-((S)-2-amino-2-cyclohexyl-acetyl)-2,3-dihydro-1H-isoindole-1-carboxylic acid (2,6-difluoro-phenyl)-amide trifluoroacetate which was used without further purification.

Step 5: To a solution of (S)-2-((S)-2-amino-2-cyclohexyl-acetyl)-2,3-dihydro-1H-isoindole-1-carboxylic acid (2,6-difluoro-phenyl)-amide trifluoroacetate (179 mg, 339 µmol, Eq: 1.00), (S)-2-(tert-butoxycarbonyl-methyl-amino)-propionic acid (64.2 mg, 339 µmol, Eq: 1.00), HATU (142 mg, 373 µmol, Eq: 1.1) in DMF (1 mL) at 0° C. was added DIEA (132 mg, 178 µL, 1.02 mmol, Eq: 3). The reaction was stirred at RT for 1 h, diluted with water and extracted with EtOAc. The combined organics were washed with water, brine, dried with MgSO$_4$ and concentrated in vacuo. The crude material was purified by flash chromatography to give ((S)-1-{(S)-1-cyclohexyl-2-[(S)-1-(2,6-difluoro-phenylcarbamoyl)-1,3-dihydro-isoindol-2-yl]-2-oxo-ethylcarbamoyl}-ethyl)-methyl-carbamic acid tert-butyl ester (174 mg) as a white foam.

Step 6: A solution of acetyl chloride (552 mg, 500 µL, 7.03 mmol, Eq: 24.2) in MeOH (2 mL) was added to a vial containing ((S)-1-{(S)-1-Cyclohexyl-2-[(S)-1-(2,6-di fluoro-phenylcarbamoyl)-1,3-dihydro-iso indol-2-yl]-2-oxo-ethylcarbamoyl}-ethyl)-methyl-carbamic acid tert-butyl ester (174 mg, 291 µmol, Eq: 1.00). The mixture was stirred at RT for 1 h. The solvent was evaporated and the resulting solid was redissolved in MeCN (3 mL) and water (1 mL). It was lyophilized to give (S)-2-[(S)-2-Cyclohexyl-2-((S)-2-methylamino-propionylamino)-acetyl]-2,3-dihydro-1H-isoindole-1-carboxylic acid (2,6-difluoro-phenyl)-amide hydrochloride (148 mg) as a white powder, m/z=499 (M+H).

Example 3

(S)-2-[(S)-2-Cyclohexyl-2-((S)-2-methylamino-propionylamino)-acetyl]-1,2,3,4-tetrahydro-isoquinoline-1-carboxylic acid (2,6-difluoro-phenyl)-amide hydrochloride

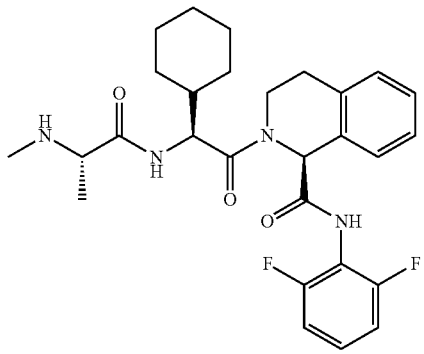 [SMILES: CN[C@@H](C)C(=O)N[C@H](C(=O)N1CCc2ccccc2[C@H]1C(=O)Nc1c(F)cccc1F)C1CCCCC1]

Step 1: To the solution of (S)-3,4-dihydro-1H-isoquinoline-1,2-dicarboxylic acid 2-tert-butyl ester (500 mg, 1.8 mmol, Eq: 1.00) and 2,6-difluoroaniline (279 mg, 2.16 mmol, Eq: 1.2) in pyridine (10.0 mL) at 0° C. was added POCl$_3$ (415 mg, 252 µL, 2.7 mmol, Eq: 1.5). The mixture was warmed to RT and stirred for 2 h. The solvent was evaporated, water was added and the mixture extracted with EtOAc. The combined organics were washed with water, brine, dried with MgSO$_4$ and concentrated in vacuo. The crude material was purified by flash chromatography to give (S)-1-(2,6-difluoro-phenylcarbamoyl)-3,4-dihydro-1H-isoquinoline-2-carboxylic acid tert-butyl ester (380 mg) as a white foam.

Step 2: To a solution of (S)-1-(2,6-difluoro-phenylcarbamoyl)-3,4-dihydro-1H-isoquinoline-2-carboxylic acid tert-butyl ester (50 mg, 129 µmol, Eq: 1.00) in CH$_2$Cl$_2$ (6 mL) was added TFA (2 mL) dropwise. The reaction was stirred at RT for 1 h. The mixture was evaporated to provide (S)-1,2,3,4-tetrahydro-isoquinoline-1-carboxylic acid (2,6-difluoro-phenyl)-amide trifluoroacetate which was used without further purification.

Step 3: To a solution of (S)-1,2,3,4-tetrahydro-isoquinoline-1-carboxylic acid (2,6-difluoro-phenyl)-amide trifluoroacetate (52 mg, 129 µmol, Eq: 1.00), (S)-2-(tert-butoxycarbonylamino)-2-cyclohexylacetic acid (33.3 mg, 129 µmol, Eq: 1.00) and HATU (54.1 mg, 142 µmol, Eq: 1.1) in DMF (300 µL) at 0° C. was added DIEA (50.1 mg, 67.7 µL, 388 µmol, Eq: 3). The reaction was stirred at RT for 1 h diluted with water and extracted with EtOAc. The combined organics were washed with water, brine, dried with MgSO$_4$ and concentrated in vacuo. The crude material was purified by flash chromatography to give {(S)-1-cyclohexyl-2-[(S)-1-(2,6-difluoro-phenylcarbamoyl)-3,4-dihydro-1H-isoquinolin-2-yl]-2-oxo-ethyl}-carbamic acid tert-butyl ester (62 mg) as a white foam.

Step 4: To a solution of {(S)-1-cyclohexyl-2-[(S)-1-(2,6-difluoro-phenylcarbamoyl)-3,4-dihydro-1H-isoquinolin-2-yl]-2-oxo-ethyl}-carbamic acid tert-butyl ester (62 mg, 118 µmol, Eq: 1.00) in CH$_2$Cl$_2$ (3 mL) was added TFA (1 mL) dropwise. The reaction was stirred at RT for 1 h. The mixture was evaporated to afford (S)-2-((S)-2-amino-2-cyclohexyl-acetyl)-1,2,3,4-tetrahydro-isoquinoline-1-carboxylic acid (2,6-difluoro-phenyl)-amide trifluoroacetate which was used without further purification.

Step 5: To a solution of (S)-2-((S)-2-amino-2-cyclohexyl-acetyl)-1,2,3,4-tetrahydro-isoquinoline-1-carboxylic acid (2,6-difluoro-phenyl)-amide trifluoroacetate (63.6 mg, 117 µmol, Eq: 1.00), (S)-2-(tert-butoxycarbonyl-methyl-amino)-propionic acid (22.2 mg, 117 µmol, Eq: 1.00), HATU (49.1 mg, 129 µmol, Eq: 1.1) in DMF (500 µL) at 0° C. was added DIEA (45.5 mg, 61.5 µL, 352 µmol, Eq: 3). The reaction was stirred at RT for 1 h diluted with water and extracted with EtOAc. The combined organics were washed with water, brine, dried with MgSO$_4$ and concentrated in vacuo. The crude material was purified by flash chromatography to give ((S)-1-{(S)-1-cyclohexyl-2-[(S)-1-(2,6-difluoro-phenylcarbamoyl)-3,4-dihydro-1H-isoquinolin-2-yl]-2-oxo-ethylcarbamoyl}-ethyl)-methyl-carbamic acid tert-butyl ester (58 mg) as a white foam.

Step 6: A solution of acetyl chloride (552 mg, 500 µL, 7.03 mmol, Eq: 74.3) in MeOH (2 mL) was added to a vial containing ((S)-1-{(S)-1-cyclohexyl-2-[(S)-1-(2,6-di fluoro-phenylcarbamoyl)-3,4-dihydro-1H-isoquinolin-2-yl]-2-oxo-ethylcarbamoyl}-ethyl)-methyl-carbamic acid tert-butyl ester (58 mg, 94.7 µmol, Eq: 1.00). The mixture was stirred at RT for 1 h. The solvent was evaporated and the resulting solid was dissolved in MeCN (3 mL) and water (1 mL) and the solution lyophilized to give (S)-2-[(S)-2-cyclohexyl-2-((S)-2-methylamino-propionylamino)-acetyl]-1,2,3,4-tetrahydro-isoquinoline-1-carboxylic acid (2,6-difluoro-phenyl)-amide hydrochloride (50 mg) as a white powder (50 mg), m/z=513 (M+H).

Example 4

(S)-2-[(S)-3-Methyl-2-((S)-2-methylamino-propionylamino)-butyryl]-1,2,3,4-tetrahydro-isoquinoline-1-carboxylic acid (2-chloro-6-fluoro-phenyl)-amide hydrochloride

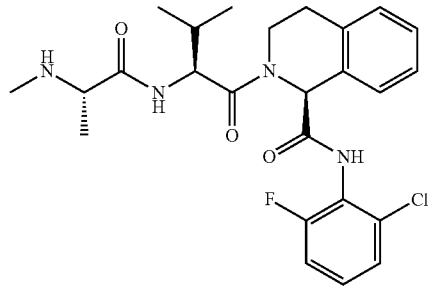 [SMILES: CN[C@@H](C)C(=O)N[C@H](C(=O)N1CCc2ccccc2[C@H]1C(=O)Nc1c(F)cccc1Cl)C(C)C]

Step 1: To the solution of (S)-3,4-dihydro-1H-isoquinoline-1,2-dicarboxylic acid 2-tert-butyl ester (100 mg, 361 µmol, Eq: 1) and 2-chloro-6-fluoroaniline (63.0 mg, 433 µmol, Eq: 1.2) in pyridine (2.00 mL) at 0° C. was added POCl$_3$ (82.9 mg, 50.4 µL, 541 µmol, Eq: 1.5). Reaction was warmed to RT and stirred for 2 h. The mixture was evaporated and water was added to the residue. The mixture was extracted with EtOAc, the combined organics were washed with water, brine, dried with MgSO$_4$ and concentrated in vacuo. The crude material was purified by flash chromatography to give (S)-1-(2-chloro-6-fluoro-phenylcarbamoyl)-3,4-dihydro-1H-isoquinoline-2-carboxylic acid tert-butyl ester (79 mg) as a white solid.

Step 2: To a solution of (S)-1-(2-chloro-6-fluoro-phenylcarbamoyl)-3,4-dihydro-1H-isoquinoline-2-carboxylic acid tert-butyl ester (78 mg, 193 µmol, Eq: 1.00) in CH$_2$Cl$_2$ (6 mL) was added TFA (2 mL) dropwise. The reaction was stirred at RT for 1 h. The mixture was evaporated to afford (S)-1,2,3,4-tetrahydro-isoquinoline-1-carboxylic acid (2-chloro-6-fluoro-phenyl)-amide trifluoroacetate which was used without further purification.

Step 3: To a solution of (S)-1,2,3,4-tetrahydro-isoquinoline-1-carboxylic acid (2-chloro-6-fluoro-phenyl)-amide trifluoroacetate (80 mg, 191 µmol, Eq: 1.00), (S)-2-(tert-butoxycarbonylamino)-3-methylbutanoic acid (41.5 mg, 191 µmol, Eq: 1.00) and HATU (79.9 mg, 210 µmol, Eq: 1.1) in DMF (500 µL) at 0° C. was added DIEA (74.1 mg, 100 µL, 573 µmol, Eq: 3). The reaction was stirred at RT for 1 h, diluted with water and extracted with EtOAc. The combined organics were washed with water, brine, dried with MgSO$_4$ and concentrated in vacuo. The crude material was purified by flash chromatography to give {(S)-1-[(S)-1-(2-chloro-6-fluoro-phenylcarbamoyl)-3,4-dihydro-1H-isoquinoline-2-carbonyl]-2-methyl-propyl}-carbamic acid tert-butyl ester (47 mg) as a white foam.

Step 4: To a solution of {(S)-1-[(S)-1-(2-chloro-6-fluoro-phenylcarbamoyl)-3,4-dihydro-1H-isoquinoline-2-carbonyl]-2-methyl-propyl}-carbamic acid tert-butyl ester (47 mg, 93.3 µmol, Eq: 1.00) in CH$_2$Cl$_2$ (3 mL) was added TFA (1 mL) dropwise. The reaction was stirred at RT for 1 h. The mixture was evaporated to provide (S)-2-((S)-2-amino-3-methyl-butyryl)-1,2,3,4-tetrahydro-isoquinoline-1-carboxylic acid (2-chloro-6-fluoro-phenyl)-amide trifluoroacetate which was used without further purification.

Step 5: To a solution of (S)-2-((S)-2-amino-3-methyl-butyryl)-1,2,3,4-tetrahydro-isoquinoline-1-carboxylic acid (2-chloro-6-fluoro-phenyl)-amide trifluoroacetate (48 mg, 92.7 µmol, Eq: 1.00), (S)-2-(tert-butoxycarbonylamino)propanoic acid (17.5 mg, 92.7 µmol, Eq: 1.00), HATU (38.8 mg, 102 µmol, Eq: 1.1) in DMF (300 µL) at 0° C. was added DIEA (35.9 mg, 48.6 µL, 278 µmol, Eq: 3). The reaction was stirred at RT for 1 h, diluted with water and extracted with EtOAc. The combined organics were washed with water, brine, dried with MgSO$_4$ and concentrated in vacuo. The crude material was purified by flash chromatography to give ((S)-1-{(S)-1-[(S)-1-(2-chloro-6-fluoro-phenylcarbamoyl)-3,4-dihydro-1H-isoquinoline-2-carbonyl]-2-methyl-propylcarbamoyl}-ethyl)-methyl-carbamic acid tert-butyl ester (36 mg) as a white foam.

Step 6: A solution of acetyl chloride (552 mg, 500 µL, 7.03 mmol, Eq: 115) in MeOH (2 mL) was added to a vial containing ((S)-1-{(S)-1-[(S)-1-(2-chloro-6-fluoro-phenylcarbamoyl)-3,4-dihydro-1H-isoquinoline-2-carbonyl]-2-methyl-propylcarbamoyl}-ethyl)-methyl-carbamic acid tert-butyl ester (36 mg, 61.1 µmol, Eq: 1.00). The mixture was stirred at RT for 1 h. The solvent was evaporated and the resulting solid was dissolved in MeCN (3 mL) and water (1 mL) which was lyophilized to give (S)-2-[(S)-3-methyl-2-((S)-2-methylamino-propionylamino)-butyryl]-1,2,3,4-tetrahydro-isoquinoline-1-carboxylic acid (2-chloro-6-fluoro-phenyl)-amide hydrochloride (30 mg) as a white powder, m/z=489 (M+H).

Example 5

6-Chloro-2-[(S)-3-methyl-2-((S)-2-methylamino-propionylamino)-butyryl]-1,2,3,4-tetrahydro-isoquinoline-1-carboxylic acid (2,6-difluoro-phenyl)-amide

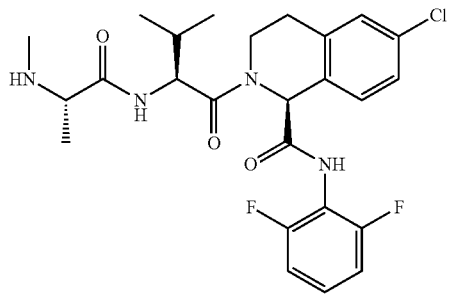 [SMILES: CN[C@@H](C)C(=O)N[C@H](C(=O)N1CCc2cc(Cl)ccc2[C@H]1C(=O)Nc1c(F)cccc1F)C(C)C]

Step 1: In a 50 mL round-bottomed flask, 2-(tert-butoxycarbonyl)-6-chloro-1,2,3,4-tetrahydroisoquinoline-1-carboxylic acid (0.5 g, 1.6 mmol, Eq: 1.00), 2,6-difluoroaniline (228 mg, 190 µl, 1.76 mmol, Eq: 1.1) and TEA (487 mg, 671 µl, 4.81 mmol, Eq: 3) were combined with DCM (10 mL) to give a colorless solution and phosphorus oxychloride (295 mg, 179 µl, 1.92 mmol, Eq: 1.2) was added. After 2 d, the reaction was diluted with DCM and washed with 1 N HCl, water and brine. The organic layer was dried over Na$_2$SO$_4$ and concentrated in vacuo to afford 0.6076 g 6-chloro-1-(2,6-difluoro-phenylcarbamoyl)-3,4-dihydro-1H-isoquinoline-2-carboxylic acid tert-butyl ester as a brown foam which was used without purification. 89.6% MS m/z 322.9 (M-BOC)

Step 2: In a 50 mL pear-shaped flask, 6-chloro-1-(2,6-difluoro-phenylcarbamoyl)-3,4-dihydro-1H-isoquinoline-2-carboxylic acid tert-butyl ester (0.6 g, 1.42 mmol, Eq: 1.00) was combined with DCM (25 mL) to give a light brown solution. TFA (4.85 g, 3.28 mL, 42.6 mmol, Eq: 30) was added. After 1 h, the reaction was concentrated, the residue dissolved in EtOAc and the mixture washed with 1 N NaOH and brine. The organic layer was dried over $Na_2SO_4$ and concentrated in vacuo to afford 0.3937 g 6-chloro-1,2,3,4-tetrahydro-isoquinoline-1-carboxylic acid (2,6-difluoro-phenyl)-amide as a brown oil which was used without purification. 86.0% MS m/z 323.0 (M+H)

Step 3: In a 100 mL round-bottomed flask, BOC-VAL-OH (315 mg, 1.45 mmol, Eq: 1.2), 6-chloro-1,2,3,4-tetrahydro-isoquinoline-1-carboxylic acid (2,6-difluoro-phenyl)-amide (0.39 g, 1.21 mmol, Eq: 1.00) and HATU (551 mg, 1.45 mmol, Eq: 1.2) were combined with DMF (10 mL) to give a brown solution and TEA (367 mg, 505 µl, 3.63 mmol, Eq: 3) was added. After 3 h, the reaction mixture was diluted with EtOAc and washed with 1:1 sat $NaHCO_3$/brine and brine. The organic layer was dried over $Na_2SO_4$ and concentrated in vacuo. The crude material was purified by flash chromatography to afford 0.3579 g {(S)-1-[6-chloro-1-(2,6-difluoro-phenylcarbamoyl)-3,4-dihydro-1H-isoquinoline-2-carbonyl]-2-methyl-propyl}-carbamic acid tert-butyl ester as light yellow foam. 56.7% MS m/z 522.0 (M+H)

Step 4: In a 100 mL pear-shaped flask, tert-butyl (2S)-1-(6-chloro-1-(2,6-difluorophenylcarbamoyl)-3,4-dihydro isoquinolin-2 (1H)-yl)-3-methyl-1-oxobutan-2-ylcarbamate (0.3579 g, 686 µmol, Eq: 1.00) was combined with DCM (20 mL) to give a light yellow solution and TFA (2.35 g, 1.58 mL, 20.6 mmol, Eq: 30) was added. After 1 h, the reaction was concentrated, the residue dissolved in EtOAc and the mixture washed with 1 N NaOH and brine. The organic layer was dried over $Na_2SO_4$ and concentrated in vacuo to afford 0.2377 g 2-((S)-2-amino-3-methyl-butyryl)-6-chloro-1,2,3,4-tetrahydro-isoquinoline-1-carboxylic acid (2,6-difluoro-phenyl)-amide as light yellow foam which was used without purification. 82.2% MS m/z 422.1 (M+H)

Step 5: In a 50 mL flask, 2-((S)-2-amino-3-methyl-butyryl)-6-chloro-1,2,3,4-tetrahydro-isoquinoline-1-carboxylic acid (2,6-difluoro-phenyl)-amide (0.2377 g, 563 µmol, Eq: 1.00), BOC—N-ME-ALA-OH (137 mg, 676 µmol, Eq: 1.2) and HATU (257 mg, 676 µmol, Eq: 1.2) were combined with DMF (6 mL) to give a light yellow solution and TEA(171 mg, 236 µl, 1.69 mmol, Eq: 3) was added. After 2 h, the reaction mixture was diluted with EtOAc and washed with brine. The organic layer was dried over $Na_2SO_4$ and concentrated in vacuo. The crude material was purified by flash chromatography to afford 0.1976 g ((S)-1-{(S)-1-[6-chloro-1-(2,6-difluoro-phenylcarbamoyl)-3,4-dihydro-1H-isoquinoline-2-carbonyl]-2-methyl-propylcarbamoyl}-ethyl)-methyl-carbamic acid tert-butyl ester as white foam. 57.8% MS m/z 607.1 (M+H)

Step 6: In a 20 mL vial, ((S)-1-{(S)-1-[6-chloro-1-(2,6-difluoro-phenylcarbamoyl)-3,4-dihydro-1H-isoquinoline-2-carbonyl]-2-methyl-propylcarbamoyl}-ethyl)-methyl-carbamic acid tert-butyl ester (0.1976 g, 325 µmol, Eq: 1.00) was combined with DCM (6 mL) to give a colorless solution and TFA (1.11 g, 752 µl, 9.76 mmol, Eq: 30) was added. After 1 h, the reaction was concentrated, the residue dissolved in EtOAc, washed with 1 N NaOH and brine. The organic layer was dried over $Na_2SO_4$ and concentrated in vacuo to afford 125.8 mg of a mixture of diastereomers as white foam. The diastereomers were separated by supercritical fluid chromatography (SFC) using a 220 mm Diacel IA column, 25% EtOH, 70 mL/min Each diastereomer was isolated and lyophilized from $MeCN/H_2O$. The first compound eluted afforded 50.2 mg of white solid. The second compound eluted afforded 47.2 mg of the title compound as white solid whose structure was assigned based on the activity in the TR-FRET assay. 57.6% MS m/z 507.2 (M+H)

Example 6

6-Fluoro-2-[(S)-3-methyl-2-((S)-2-methylamino-propionylamino)-butyryl]-1,2,3,4-tetrahydro-isoquinoline-1-carboxylic acid (2,6-difluoro-phenyl)-amide

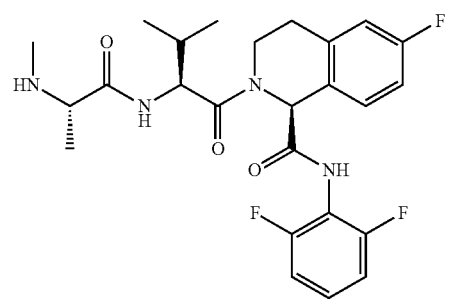 [SMILES: CN[C@@H](C)C(=O)N[C@H](C(=O)N1CCc2cc(F)ccc2[C@H]1C(=O)Nc1c(F)cccc1F)C(C)C]

Step 1: In a 50 mL round-bottomed flask, 6-fluoro-1,2,3,4-tetrahydroisoquinoline-1-carboxylic acid hydrochloride (500 mg, 2.16 mmol, Eq: 1.00) and 2 N NaOH (3.24 mL, 6.48 mmol, Eq: 3) were combined with t-BuOH (3.00 mL) to give a light brown solution and BOC-anhydride (565 mg, 601 µl, 2.59 mmol, Eq: 1.2) was added. After stirring 18 h, the reaction was diluted with water and extracted ether. The aqueous layer was acidified with saturated $KHSO_4$ and extracted with EtOAc. The combined organic extracts were washed with brine, dried over $Na_2SO_4$, filtered and concentrated to give 0.6448 g 6-fluoro-3,4-dihydro-1H-isoquinoline-1,2-dicarboxylic acid 2-tert-butyl ester as white foam which was used without purification. 100% MS m/z 193.9 (M-BOC)

Step 2: To a solution of 6-fluoro-3,4-dihydro-1H-isoquinoline-1,2-dicarboxylic acid 2-tert-butyl ester (0.37 g, 1.25 mmol, Eq: 1.00) and 2,6-difluoroaniline (194 mg, 162 µl, 1.5 mmol, Eq: 1.2) in Pyridine (7 mL) at 0° C. was added phosphorus oxychloride (288 mg, 175 µl, 1.88 mmol, Eq: 1.5). The reaction was warmed to RT, stirred for 18 h, diluted with water and extracted with EtOAc. The combined organics were washed with 1 N HCl, water, brine, dried with $Na_2SO_4$ and concentrated in vacuo. The crude material was purified by flash chromatography to afford 0.2181 g 1-(2,6-difluoro-phenylcarbamoyl)-6-fluoro-3,4-dihydro-1H-isoquinoline-2-carboxylic acid tert-butyl ester as white foam. 42.8% MS m/z 428.9 (M+H)

Step 3: In a 50 mL round-bottomed flask, 1-(2,6-difluoro-phenylcarbamoyl)-6-fluoro-3,4-dihydro-1H-isoquinoline-2-carboxylic acid tert-butyl ester (0.218 g, 536 µmol, Eq: 1.00) was combined with DCM (7.00 mL) to give a colorless solution and TFA (1.83 g, 1.24 mL, 16.1 mmol, Eq: 30) was added. After 1 h, the mixture was concentrated to afford 0.2867 g 6-fluoro-1,2,3,4-tetrahydro-isoquinoline-1-carboxylic acid (2,6-difluoro-phenyl)-amide trifluoroacetate as a yellow oil which was used without purification. 127% MS m/z 307.1 (M+H)

Step 4: In a 50 mL round-bottomed flask, BOC-VAL-OH (140 mg, 643 µmol, Eq: 1.2) and 6-fluoro-1,2,3,4-tetrahydro-isoquinoline-1-carboxylic acid (2,6-difluoro-phenyl)-amide trifluoroacetate (225 mg, 536 μmol, Eq: 1.00) were combined with DMF (3 mL) to give a light yellow solution and TEA (217 mg, 299 μl, 2.14 mmol, Eq: 4) was added. To this solution was added a solution of HBTU (244 mg, 643 μmol, Eq: 1.2) and HOBT.H₂O (98.5 mg, 643 μmol, Eq: 1.2) in DMF (3 mL). After 2 h, the reaction mixture was diluted with EtOAc and washed with 1:1 sat NaHCO₃/brine, brine and the organic layer was dried over Na₂SO₄ and concentrated in vacuo. The crude material was purified by flash chromatography to afford 97.8 mg {(S)-1-[1-(2,6-difluoro-phenylcarbamoyl)-6-fluoro-3,4-dihydro-1H-isoquinoline-2-carbonyl]-2-methyl-propyl}-carbamic acid tert-butyl ester as white foam. 36.1% MS m/z 506.0 (M+H)

Step 5: In a 20 mL vial, {(S)-1-[1-(2,6-Difluoro-phenylcarbamoyl)-6-fluoro-3,4-dihydro-1H-isoquinoline-2-carbonyl]-2-methyl-propyl}-carbamic acid tert-butyl ester (97.8 mg, 193 μmol, Eq: 1.00) was combined with DCM (4 mL) to give a colorless solution and TFA (662 mg, 447 μl, 5.8 mmol, Eq: 30) was added. After 1 h, the mixture was concentrated to afford 0.1346 g 2-((S)-2-amino-3-methyl-butyryl)-6-fluoro-1,2,3,4-tetrahydro-isoquinoline-1-carboxylic acid (2,6-difluoro-phenyl)-amide trifluoroacetate as a light brown oil which was used without purification. 134% MS m/z 406.1 (M+H)

Step 6: In a 20 mL vial, 2-((S)-2-Amino-3-methyl-butyryl)-6-fluoro-1,2,3,4-tetrahydro-isoquinoline-1-carboxylic acid (2,6-difluoro-phenyl)-amide trifluoroacetate (100 mg, 193 μmol, Eq: 1.00), BOC—N-ME-ALA-OH (47.1 mg, 232 μmol, Eq: 1.2) and HATU (88.1 mg, 232 μmol, Eq: 1.2) were combined with DMF (3 mL) to give a light brown solution and TEA (97.6 mg, 135 μl, 965 μmol, Eq: 5) was added. After 2.5 h, the mixture was diluted with EtOAc and washed with brine. The organic layer was dried over Na₂SO₄ and concentrated in vacuo. The crude material was purified by flash chromatography to afford 77.1 mg ((S)-1-{(S)-1-[1-(2,6-difluoro-phenylcarbamoyl)-6-fluoro-3,4-dihydro-1H-isoquinoline-2-carbonyl]-2-methyl-propylcarbamoyl}-ethyl)-methyl-carbamic acid tert-butyl ester as a white solid. 67.6% MS m/z 591.1 (M+H)

Step 7: In a 20 mL vial, ((S)-1-{(S)-1-[1-(2,6-difluoro-phenylcarbamoyl)-6-fluoro-3,4-dihydro-1H-isoquinoline-2-carbonyl]-2-methyl-propylcarbamoyl}-ethyl)-methyl-carbamic acid tert-butyl ester (77.1 mg, 131 μmol, Eq: 1.00) was combined with DCM (3.00 mL) to give a colorless solution and TFA (447 mg, 302 μl, 3.92 mmol, Eq: 30) was added. After 30 min the mixture was concentrated, the residue dissolved in EtOAc and washed with 1 N NaOH, water, dried over Na₂SO₄ and concentrated in vacuo to give 47.9 mg of a mixture of diastereomers as a white foam. Each diastereomer was isolated and lyophilized from MeCN/H₂O. The first compound eluted afforded 22.6 mg of white solid. The second compound eluted afforded 13.7 mg of the title compound as a white solid whose structure was assigned based on the activity in the TR-FRET assay. 21.4% MS m/z 491.3 (M+H)

The compounds listed in Table 1 below were prepared following the procedures described above for Example 1, where the amines listed in the table were used in place of 2,6-difluoroaniline in Step 1.

TABLE 1

| Example | Amine | Final Product | m/z (M + H) |
|---------|-------|---------------|-------------|
| Example 7 | 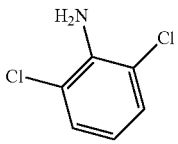 | 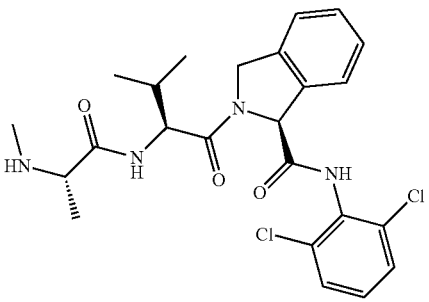 [SMILES: CN[C@@H](C)C(=O)N[C@H](C(=O)N1Cc2ccccc2[C@H]1C(=O)Nc1c(Cl)cccc1Cl)C(C)C] | 491 |
| Example 8 | 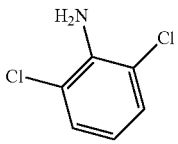 | 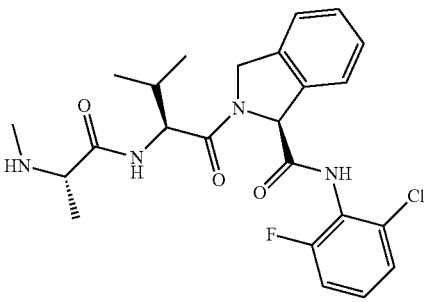 [SMILES: CN[C@@H](C)C(=O)N[C@H](C(=O)N1Cc2ccccc2[C@H]1C(=O)Nc1c(F)cccc1Cl)C(C)C] | 475 |

TABLE 1-continued
| Example | Amine | Final Product | m/z (M + H) |
|---|---|---|---|
| Example 9 | 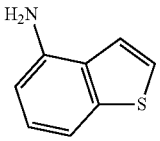 | 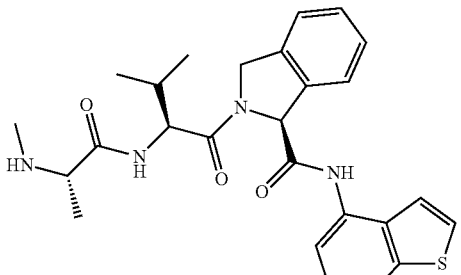 | 479 |
| Example 18 | 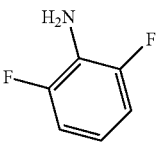 | 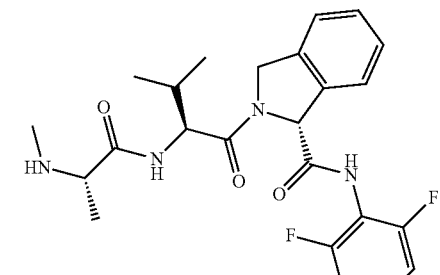 | 459 |
| Example 21 | 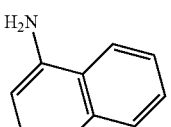 | 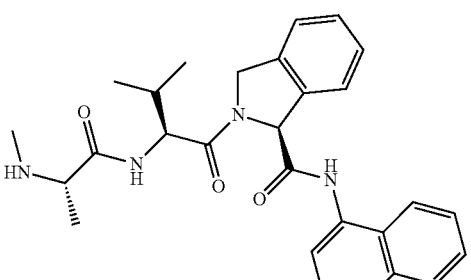 | 473 |
| Example 22 | 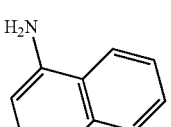 | 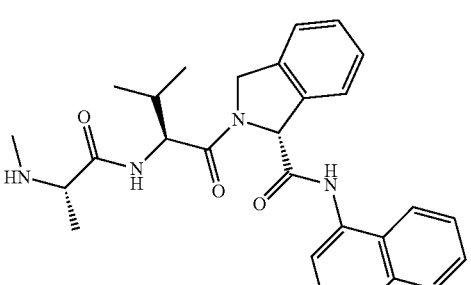 | 473 |
| Example 23 | 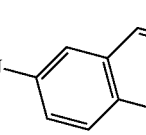 | 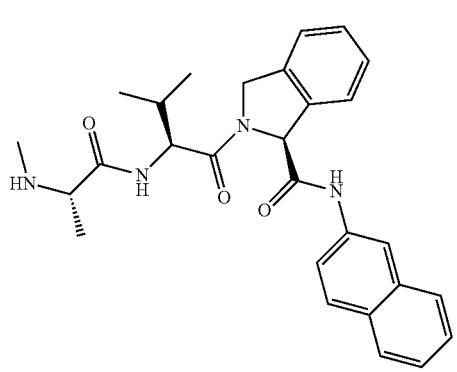 [SMILES: CN[C@@H](C)C(=O)N[C@H](C(=O)N1Cc2ccccc2[C@H]1C(=O)Nc1ccc2ccccc2c1)C(C)C] | 473 |

TABLE 1-continued

| Example | Amine | Final Product | m/z (M + H) |
|---|---|---|---|
| Example 24 | 2-fluoroaniline | | 441 |
| Example 26 | 2-chloroaniline | | 457 |
| Example 27 | 5-amino-1,2,3,4-tetrahydronaphthalene | | 477 |
| Example 28 | 8-aminoquinoline | | 474 |
| Example 30 | 4-amino-1-methylindole | | 476 |

TABLE 1-continued

| Example | Amine | Final Product | m/z (M + H) |
|---|---|---|---|
| Example 47 | 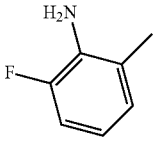 | 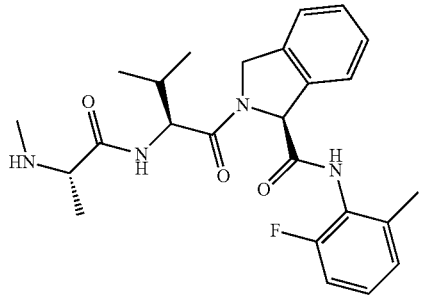 | 455 |

The compounds listed in Table 2 below were prepared following the procedures described above for Example 1, where the amines listed in the table were used in place of 2,6-difluoroaniline in Step 1 and the separation of diastereomers described in Step 3 was omitted.

TABLE 2

| Example | Amine | Final Product | m/z (M + H) |
|---|---|---|---|
| Example 16 | 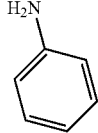 | 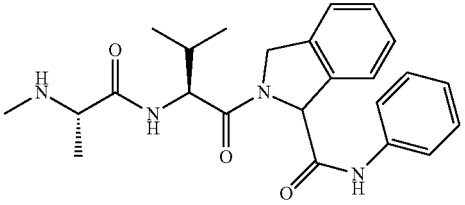 [SMILES: CN[C@@H](C)C(=O)N[C@H](C(=O)N1Cc2ccccc2C1C(=O)Nc1ccccc1)C(C)C] | 423 |
| Example 17 | 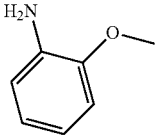 | 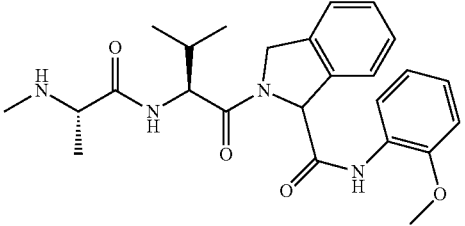 [SMILES: CN[C@@H](C)C(=O)N[C@H](C(=O)N1Cc2ccccc2C1C(=O)Nc1ccccc1OC)C(C)C] | 453 |
| Example 19 | 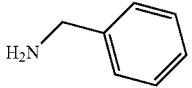 | 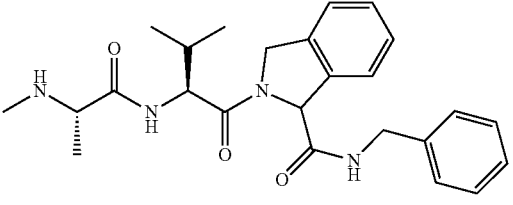 [SMILES: CN[C@@H](C)C(=O)N[C@H](C(=O)N1Cc2ccccc2C1C(=O)NCc1ccccc1)C(C)C] | 437 |
| Example 20 | 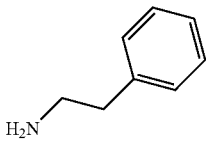 | 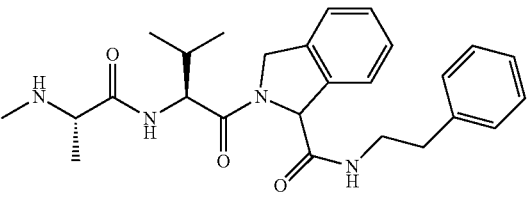 [SMILES: CN[C@@H](C)C(=O)N[C@H](C(=O)N1Cc2ccccc2C1C(=O)NCCc1ccccc1)C(C)C] | 451 |

TABLE 2-continued
| Example | Amine | Final Product | m/z (M + H) |
|---|---|---|---|
| Example 29 | 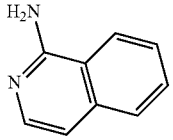 [SMILES: Nc1nccc2ccccc12] | 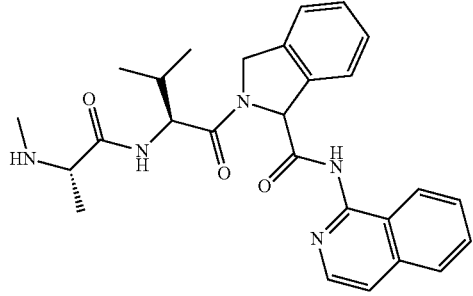 [SMILES: CN[C@@H](C)C(=O)N[C@H](C(=O)N1Cc2ccccc2C1C(=O)Nc1nccc2ccccc12)C(C)C] | 474 |
The compounds listed in Table 3 were prepared following the procedures described above for Example 2, where the carboxylic acids listed in the table were used in place of (S)-2-(tert-butoxycarbonylamino)-2-cyclohexylacetic acid in Step 3.
TABLE 3
| Example | Acid | Final Product | m/z (M + H) |
|---|---|---|---|
| Example 10 | 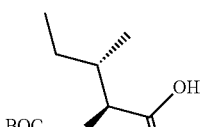 | 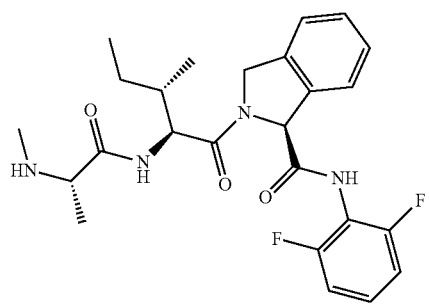 [SMILES: CC[C@H](C)[C@H](NC(=O)[C@H](C)NC)C(=O)N1Cc2ccccc2[C@H]1C(=O)Nc1c(F)cccc1F] | 473 |
| Example 11 | 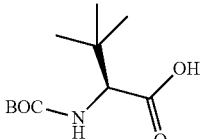 | 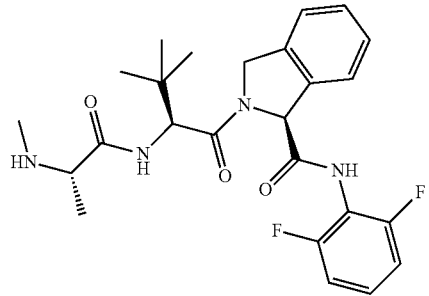 [SMILES: CN[C@@H](C)C(=O)N[C@H](C(=O)N1Cc2ccccc2[C@H]1C(=O)Nc1c(F)cccc1F)C(C)(C)C] | 473 |
| Example 12 | 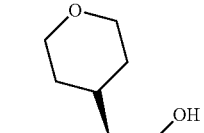 | 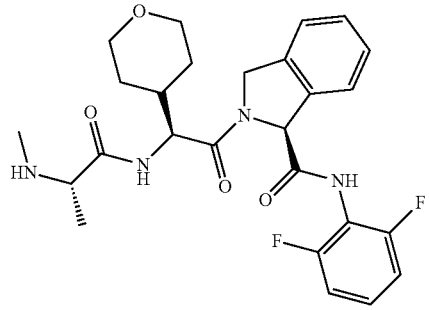 [SMILES: CN[C@@H](C)C(=O)N[C@H](C(=O)N1Cc2ccccc2[C@H]1C(=O)Nc1c(F)cccc1F)C1CCOCC1] | 501 |

TABLE 3-continued
| Example | Acid | Final Product | m/z (M + H) |
|---|---|---|---|
| Example 13 | 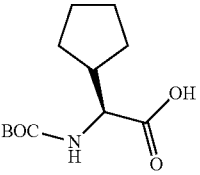 [SMILES: CC(C)(C)OC(=O)N[C@H](C(=O)O)C1CCCC1] | 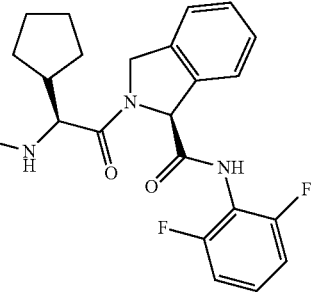 | 485 |
| Example 32 | 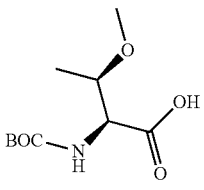 [SMILES: CO[C@H](C)[C@H](NC(=O)OC(C)(C)C)C(=O)O] | 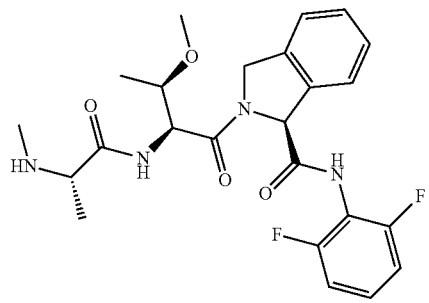 [SMILES: CN[C@@H](C)C(=O)N[C@H](C(=O)N1Cc2ccccc2[C@H]1C(=O)Nc1c(F)cccc1F)[C@@H](C)OC] | 475 |
| Example 33 | 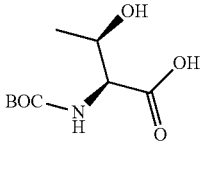 | 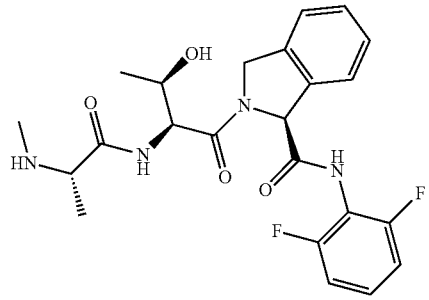 [SMILES: CN[C@@H](C)C(=O)N[C@H](C(=O)N1Cc2ccccc2[C@H]1C(=O)Nc1c(F)cccc1F)[C@@H](C)O] | 461 |
| Example 34 | 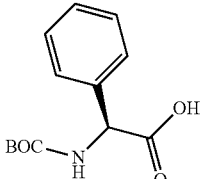 | 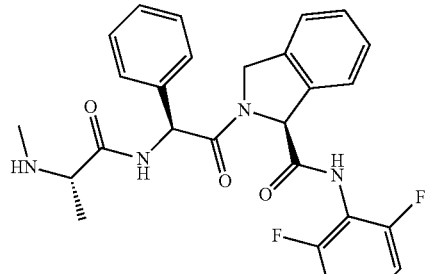 | 493 |
| Example 35 | 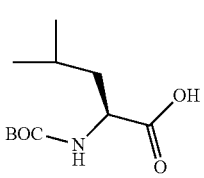 | 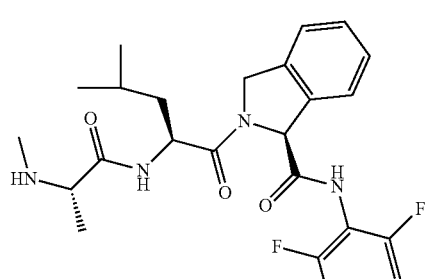 | 473 |

TABLE 3-continued
| Example | Acid | Final Product | m/z (M + H) |
|---|---|---|---|
| Example 40 | | | 521 |
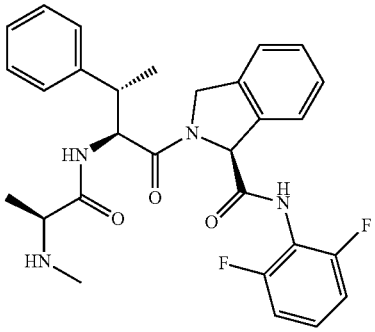 [SMILES: CN[C@@H](C)C(=O)N[C@H](C(=O)N1Cc2ccccc2[C@H]1C(=O)Nc1c(F)cccc1F)[C@@H](C)c1ccccc1]
The compounds listed in Table 4 below were prepared following the procedures described above for Example 3, where the carboxylic acids listed in the table were used in place of (S)-2-(tert-butoxycarbonylamino)-2-cyclohexylacetic acid in Step 3.
TABLE 4
| Example | Acid | Final Product | m/z (M + H) |
|---|---|---|---|
| Example 14 | | | 515 |
| Example 15 | | | 487 |

TABLE 4-continued

| Example | Acid | Final Product | m/z (M + H) |
|---------|------|---------------|-------------|
| Example 25 | | | 473 |
| Example 37 | | | 499 |
| Example 38 | | | 487 |
| Example 39 | | | 489 |

The compound listed in Table 5 below was prepared following the procedures described above for Example 4, where the amine listed in the table was used in place of 2-chloro-6-fluoroaniline in Step 1.

TABLE 5

| Example | Amine | Final Product | m/z (M + H) |
|---------|-------|---------------|-------------|
| Example 36 | 2,6-dichloroaniline | (structure shown) | 505 |

The compounds listed in Table 6 below were prepared following the procedures described above for Example 5, where the 1,2,3,4-tetrahydro-isoquinoline-1-carboxylic acids listed in the table were used in place of 2-(tert-butoxycarbonyl)-6-chloro-1,2,3,4-tetrahydroisoquinoline-1-carboxylic acid in Step 1.

TABLE 6

| Example | Acid | Final Product | m/z (M + H) |
|---------|------|---------------|-------------|
| Example 44 | (structure shown) | (structure shown) | 507 |
| Example 45 | (structure shown) | (structure shown) | 507 |
| Example 46 | (structure shown) | (structure shown) | 507 |

The compounds listed in Table 7 below were prepared following the procedures described above for Example 6, where the 1,2,3,4-tetrahydro-isoquinoline-1-carboxylic acids listed in the table were used in place of 2-(tert-butoxycarbonyl)-6-chloro-1,2,3,4-tetrahydroisoquinoline-1-carboxylic acid in Step 1.
TABLE 7
| Example | Acid | Final Product | m/z (M + H) |
|---------|------|---------------|-------------|
| Example 41 | 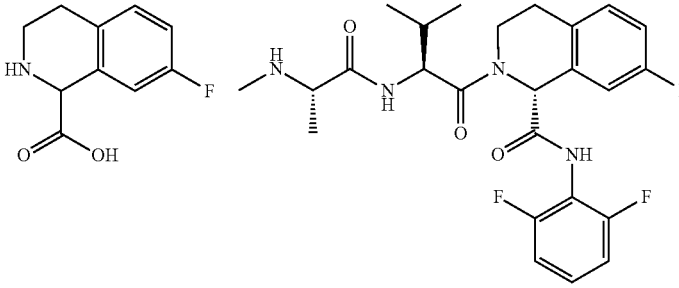 | 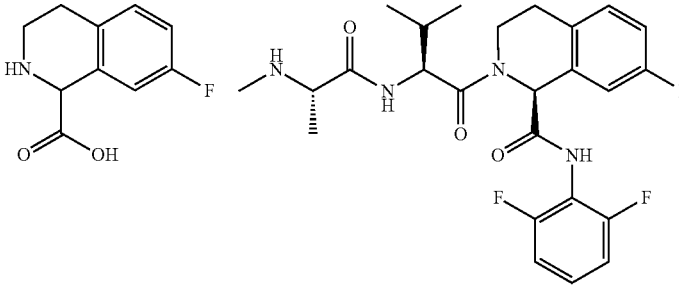 | 491 |
| Example 42 | 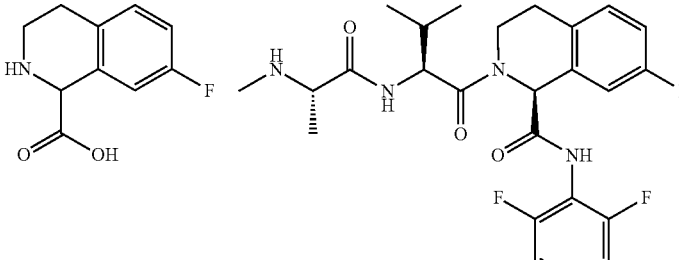 | 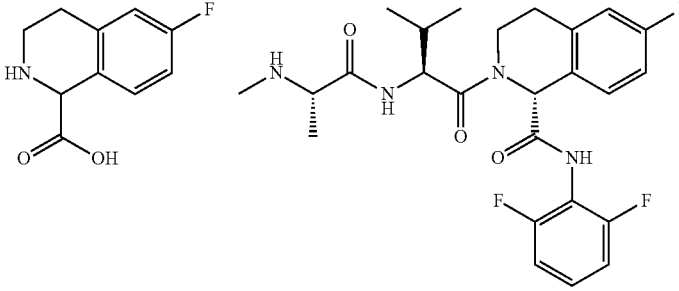 | 491 |
| Example 43 | 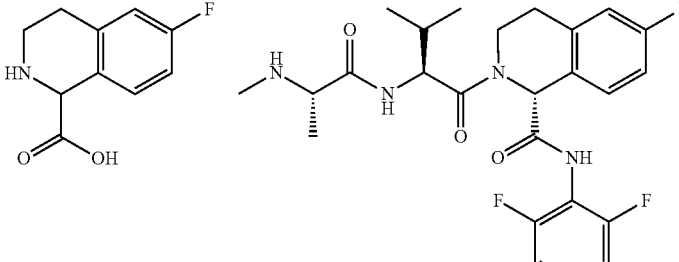 |  | 491 |

Example 31

(S)-2-[(S)-3-Methyl-2-((S)-2-methylamino-propionylamino)-butyryl]-1,2,3,4-tetrahydro-isoquinoline-3-carboxylic acid (2,6-difluoro-phenyl)-amide

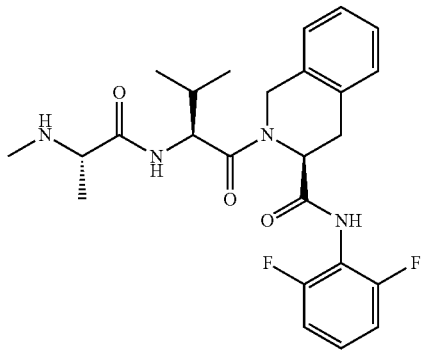 [SMILES: CN[C@@H](C)C(=O)N[C@H](C(=O)N1Cc2ccccc2C[C@H]1C(=O)Nc1c(F)cccc1F)C(C)C]

Step 1: To a solution of (S)-2-(tert-butoxycarbonyl)-1,2,3,4-tetrahydroisoquinoline-3-carboxylic acid (200 mg, 721 µmol, Eq: 1.00) and 2,6-difluoroaniline (121 mg, 101 µL, 938 µmol, Eq: 1.3) in pyridine (2 mL) at 0° C. was added dropwise phosphorus oxychloride (166 mg, 101 µL, 1.08 mmol, Eq: 1.5). The cooling bath was removed and the reaction stirred at RT overnight. The reaction mixture was concentrated in vacuo and water was added to the residue. The resulting mixture was extracted with EtOAc and the combined organic layers were washed with 0.1 M HCl, 0.1 M NaOH, and brine and concentrated in vacuo. The crude material was purified by flash chromatography to give (S)-tert-butyl 3-(2,6-difluorophenylcarbamoyl)-3,4-dihydroisoquinoline-2(1H)-carboxylate as a colorless oil (90 mg), m/z=411 (M+Na).

Step 2: To a solution of (S)-tert-butyl 3-(2,6-difluorophenylcarbamoyl)-3,4-dihydroisoquinoline-2(1H)-carboxylate (90 mg, 232 µmol, Eq: 1.00) in DCM (2 mL) was added TFA (2 mL, 26.0 mmol, Eq: 112) and the resulting solution stirred at RT for 1 h. The reaction mixture was concentrated in vacuo and the residue azeotroped with n-heptanes to give (S)—N-(2,6-difluorophenyl)-1,2,3,4-tetrahydroisoquinoline-3-carboxamide trifluoroacetate which was used without purification (93 mg), m/z=289 (M+H).

Step 3: To a solution of (S)-2-(tert-butoxycarbonylamino)-3-methylbutanoic acid (60 mg, 277 µmol, Eq: 1.2) and DIEA (120 µL, 693 µmol, Eq: 3) in DMF (1 mL) was added HATU (105 mg, 277 µmol, Eq: 1.2) and the resulting solution stirred at RT for 15 min. (S)—N-(2,6-Difluorophenyl)-1,2,3,4-tetrahydroisoquinoline-3-carboxamide trifluoroacetate (93 mg, 231 µmol, Eq: 1.00) in DMF (1 mL) was then added and stirring was continued at rt. After 1 h, the reaction mixture was diluted with EtOAc and washed with 0.1 M NaOH, 0.1 M HCl, and brine. The organic layer was concentrated in vacuo and the residue azeotroped with n-heptanes to give tert-butyl (S)-1-((S)-3-(2,6-difluorophenylcarbamoyl)-3,4-dihydro isoquinolin-2 (1H)-yl)-3-methyl-1-oxobutan-2-ylcarbamate as a white solid which was used without purification (130 mg), m/z=488 (M+H).

Step 4: To a solution of tert-butyl (S)-1-((S)-3-(2,6-difluorophenylcarbamoyl)-3,4-dihydroisoquinolin-2(1H)-yl)-3-methyl-1-oxobutan-2-ylcarbamate (0.11 g, 226 µmol, Eq: 1.00) in DCM (2 mL) was added TFA (2.96 g, 2 mL, 26.0 mmol, Eq: 115) and the resulting solution was stirred at RT for 1 h. The reaction mixture was concentrated in vacuo and the residue azeotroped with n-heptanes to give (S)-2-((S)-2-amino-3-methylbutanoyl)-N-(2,6-difluorophenyl)-1,2,3,4-tetrahydroisoquinoline-3-carboxamide trifluoroacetate which was used without purification (0.11 g).

Step 5: To a solution of (S)-2-(tert-butoxycarbonyl(methyl)amino)propanoic acid (53.5 mg, 263 µmol, Eq: 1.2) and DIEA (190 µL, 1.1 mmol, Eq: 5) in DMF (2 mL) was added HATU (100 mg, 263 µmol, Eq: 1.2). The mixture was stirred for 20 min. and (S)-2-((S)-2-amino-3-methylbutanoyl)-N-(2,6-difluorophenyl)-1,2,3,4-tetrahydro isoquinoline-3-carboxamide trifluoroacetate (0.11 g, 219 µmol, Eq: 1.00) in DMF (1 mL) was added and the resulting solution stirred at RT overnight.

The reaction mixture was diluted with EtOAc, washed with 0.1 M HCl, 0.1 M NaOH, and brine. The organic layer was concentrated in vacuo and the residue azeotroped with n-heptanes. The resulting material was purified by flash chromatography to give tert-butyl (S)-1-((S)-1-((S)-3-(2,6-difluorophenylcarbamoyl)-3,4-dihydroisoquinolin-2 (1H)-yl)-3-methyl-1-oxobutan-2-ylamino)-1-oxopropan-2-yl(methyl)carbamate as a colorless oil (0.14 g), m/z=573 (M+H).

Step 6: To a solution of tert-butyl (S)-1-((S)-1-((S)-3-(2,6-difluorophenylcarbamoyl)-3,4-dihydro isoquinolin-2 (1H)-yl)-3-methyl-1-oxobutan-2-ylamino)-1-oxopropan-2-yl(methyl)carbamate (138 mg, 241 µmol, Eq: 1.00) in DCM (2 mL) was added TFA (2.96 g, 2 mL, 26.0 mmol, Eq: 108) and the resulting solution stirred at RT for 1 h. The mixture was concentrated in vacuo, saturated NaHCO$_3$ was added to the residue and the resulting mixture extracted with DCM. The combined extracts were dried over Na$_2$SO$_4$ and concentrated in vacuo. The residue was treated with ether/hexanes to give (S)-2-[(S)-3-methyl-2-((S)-2-methylamino-propionylamino)-butyryl]-1,2,3,4-tetrahydro-isoquinoline-3-carboxylic acid (2,6-difluoro-phenyl)-amide as a white solid which was used without purification (70 mg), m/z=473 (M+H).

Example 48

Biochemical Assays

TR-FRET Assay for BIR2 and BIR3

The ability of a test compound to inhibit the binding of BIR2 and/or BIR3 domains of the XIAP protein to Peptide A (a SMAC-derived peptide described below) evidences that the test compound acts as a SMAC-mimetic resulting in reactivation of a cell's apoptotic pathway.

The peptide AVPIAQKSEK-(ε-biotin)-OH 1:2 TFA ("Peptide A") was identified as a substrate for the TR-FRET assay by screening the 6× Histidine-tagged BIR2 domain and BIR3 domain of XIAP against a set of 29 peptides synthesized based on sequences reported by Sweeny et al. (*Biochemistry*, 2006, 45, 14740 14748). The peptides were labeled with the fluorescent tags FITC or TAMRA and Kd values were determined by fluorescence polarization assay. The sequence AVPIAQKSEK was identified as optimal for using in an assay. The peptide sequence was derivatized with biotin to provide AVPIAQKSEK-(ε-biotin)-OH 1:2 TFA as the substrate for the TR-FRET assay.

The XIAP protein sequence was obtained from the SWISS-PROT protein sequence database and the BIR2 and BIR3 domains were derived from that. The sequence of the BIR2 domain used for the TR-FRET assay is

MRHHHHHHRDHFALDRPSETHADYLLRTGQVVDISDTIYPRNPAMYSEEA

RLKSFQNWPDYAHLTPRELASAGLYYTGIGDQVQCFACGGKLKNWEPGDR

AWSEHRRHFPNCFFVLGRNLNIRSE.

The sequence of the BIR3 domain used for the TR-FRET assay is

MRHHHHHHRSDAVSSDRNFPNSTNLPRNPSMADYEARIFTFGTWIYSVNK

EQLARAGFYALGEGDKVKCFHCGGGLTDWKPSEDPWEQHAKWYPGCKYLL

EQKGQEYINNIHLTHSLEECLVRTT.

Ten nanomolar of 6× Histidine-tagged BIR2 domain, corresponding to amino acids 124-240 of XIAP, or BIR3 domain, corresponding to amino acids 241-356 of XIAP, was mixed with 20 nM of the peptide AVPIAQKSEK-(ε-biotin)-OH 1:2 TFA, in the presence of 50 mM Tris-Cl, pH 7.5, 100 mM NaCl, 1 mM dithiothreitol (DTT) and 0.1 mg/mL bovine serum albumin (BSA). Following a 45 min. incubation at 37° C., Europium-Streptavidin and Allophycocyanin conjugated anti-Histidine antibody were added to a final concentration of 1.5 nM and 15 nM, respectively. Time-resolved fluorescence resonance energy transfer (TR-FRET) signals were measured 1 hour later at room temperature. Test compound potency was assessed at 10 serially diluted concentrations. Percentage of inhibition at each concentration was determined to generate an $IC_{50}$ value for each test compound.

These values are listed below in Table 8.

TABLE 8

| Example | Name | BIR2 IC50 (μM) | BIR3 IC50 (μM) |
|---|---|---|---|
| Example 1 | (S)-2-[(S)-3-Methyl-2-((S)-2-methylamino-propionylamino)-butyryl]-2,3-dihydro-1H-isoindole-1-carboxylic acid (2,6-difluoro-phenyl)-amide hydrochloride | 0.012 | 23.69 |
| Example 2 | (S)-2-[(S)-2-Cyclohexyl-2-((S)-2-methylamino-propionylamino)-acetyl]-2,3-dihydro-1H-isoindole-1-carboxylic acid (2,6-difluoro-phenyl)-amide hydrochloride | 0.009 | 14.44 |
| Example 3 | (S)-2-[(S)-2-Cyclohexyl-2-((S)-2-methylamino-propionylamino)-acetyl]-1,2,3,4-tetrahydro-isoquinoline-1-carboxylic acid (2,6-difluoro-phenyl)-amide hydrochloride | 0.026 | 46.8 |
| Example 4 | (S)-2-[(S)-3-Methyl-2-((S)-2-methylamino-propionylamino)-butyryl]-1,2,3,4-tetrahydro-isoquinoline-1-carboxylic acid (2-chloro-6-fluoro-phenyl)-amide hydrochloride | 0.006 | 9.942 |
| Example 5 | 6-Chloro-2-[(S)-3-methyl-2-((S)-2-methylamino-propionylamino)-butyryl]-1,2,3,4-tetrahydro-isoquinoline-1-carboxylic acid (2,6-difluoro-phenyl)-amide | 0.021 | 38.3 |
| Example 6 | 6-Fluoro-2-[(S)-3-methyl-2-((S)-2-methylamino-propionylamino)-butyryl]-1,2,3,4-tetrahydro-isoquinoline-1-carboxylic acid (2,6-difluoro-phenyl)-amide | 0.025 | >54.8 |
| Example 7 | (S)-N-(2,6-dichlorophenyl)-2-((S)-3-methyl-2-((S)-2-(methylamino)propanamido)butanoyl)isoindoline-1-carboxamide hydrochloride | 0.009 | 7.746 |
| Example 8 | (S)-N-(2-chloro-6-fluorophenyl)-2-((S)-3-methyl-2-((S)-2-(methylamino)propanamido)butanoyl)isoindoline-1-carboxamide hydrochloride | 0.010 | 4.304 |
| Example 9 | (S)-N-(benzo[b]thiophen-4-yl)-2-((S)-3-methyl-2-((S)-2-(methylamino)propanamido)butanoyl)isoindoline-1-carboxamide hydrochloride | 0.043 | 14.83 |
| Example 10 | (S)-N-(2,6-difluorophenyl)-2-((2S,3S)-3-methyl-2-((S)-2-(methylamino)propanamido)pentanoyl)isoindoline-1-carboxamide hydrochloride | 0.006 | 15.2 |
| Example 11 | (S)-N-(2,6-difluorophenyl)-2-((S)-3,3-dimethyl-2-((S)-2-(methylamino)propanamido)butanoyl)isoindoline-1-carboxamide hydrochloride | 0.013 | >54.8 |
| Example 12 | (S)-N-(2,6-difluorophenyl)-2-((S)-2-((S)-2-(methylamino)propanamido)-2-(tetrahydro-2H-pyran-4-yl)acetyl)isoindoline-1-carboxamide hydrochloride | 0.014 | |
| Example 13 | (S)-2-((S)-2-cyclopentyl-2-((S)-2-(methylamino)propanamido)acetyl)-N-(2,6-difluorophenyl)isoindoline-1-carboxamide hydrochloride | 0.023 | 19.81 |
| Example 14 | (S)-N-(2,6-difluorophenyl)-2-((S)-2-((S)-2-(methylamino)propanamido)-2-(tetrahydro-2H-pyran-4-yl)acetyl)-1,2,3,4-tetrahydroisoquinoline-1-carboxamide hydrochloride | 0.016 | 43.9 |
| Example 15 | (S)-N-(2,6-difluorophenyl)-2-((2S,3S)-3-methyl-2-((S)-2-(methylamino)propanamido)pentanoyl)-1,2,3,4-tetrahydroisoquinoline-1-carboxamide hydrochloride | 0.013 | >54.8 |
| Example 16 | 2-((S)-3-methyl-2-((S)-2-(methylamino)propanamido)butanoyl)-N-phenylisoindoline-1-carboxamide hydrochloride | 0.233 | >54.8 |

TABLE 8-continued

| Example | Name | BIR2 IC50 (μM) | BIR3 IC50 (μM) |
|---|---|---|---|
| Example 17 | N-(2-methoxyphenyl)-2-((S)-3-methyl-2-((S)-2-(methylamino)propanamido)butanoyl)isoindoline-1-carboxamide hydrochloride | 0.177 | 3.364 |
| Example 18 | (S)-N-(2,6-difluorophenyl)-2-((S)-3-methyl-2-((S)-2-(methylamino)propanamido)butanoyl)isoindoline-1-carboxamide hydrochloride | 0.139 | >54.8 |
| Example 19 | N-benzyl-2-((S)-3-methyl-2-((S)-2-(methylamino)propanamido)butanoyl)isoindoline-1-carboxamide hydrochloride | 0.210 | 0.692 |
| Example 20 | 2-((S)-3-methyl-2-((S)-2-(methylamino)propanamido)butanoyl)-N-phenethylisoindoline-1-carboxamide hydrochloride | 0.810 | 1.914 |
| Example 21 | (S)-2-((S)-3-methyl-2-((S)-2-(methylamino)propanamido)butanoyl)-N-(naphthalen-1-yl)isoindoline-1-carboxamide hydrochloride | 0.005 | 2.466 |
| Example 22 | (R)-2-((S)-3-methyl-2-((S)-2-(methylamino)propanamido)butanoyl)-N-(naphthalen-1-yl)isoindoline-1-carboxamide hydrochloride | 2.794 | >54.8 |
| Example 23 | (S)-2-((S)-3-methyl-2-((S)-2-(methylamino)propanamido)butanoyl)-N-(naphthalen-2-yl)isoindoline-1-carboxamide hydrochloride | 0.117 | 19.76 |
| Example 24 | (S)-N-(2-fluorophenyl)-2-((S)-3-methyl-2-((S)-2-(methylamino)propanamido)butanoyl)isoindoline-1-carboxamide hydrochloride | 0.022 | 17.31 |
| Example 25 | (S)-N-(2,6-difluorophenyl)-2-((S)-3-methyl-2-((S)-2-(methylamino)propanamido)butanoyl)-1,2,3,4-tetrahydroisoquinoline-1-carboxamide hydrochloride | 0.027 | >54.8 |
| Example 26 | (S)-N-(2-chlorophenyl)-2-((S)-3-methyl-2-((S)-2-(methylamino)propanamido)butanoyl)isoindoline-1-carboxamide hydrochloride | 0.021 | 6.076 |
| Example 27 | (S)-2-((S)-3-methyl-2-((S)-2-(methylamino)propanamido)butanoyl)-N-(5,6,7,8-tetrahydronaphthalen-1-yl)isoindoline-1-carboxamide hydrochloride | 0.106 | 14.84 |
| Example 28 | (S)-2-((S)-3-methyl-2-((S)-2-(methylamino)propanamido)butanoyl)-N-(quinolin-8-yl)isoindoline-1-carboxamide hydrochloride | 6.589 | 27.93 |
| Example 29 | N-(isoquinolin-1-yl)-2-((S)-3-methyl-2-((S)-2-(methylamino)propanamido)butanoyl)isoindoline-1-carboxamide hydrochloride | 0.345 | 16.03 |
| Example 30 | (S)-N-(1-methyl-1H-indol-4-yl)-2-((S)-3-methyl-2-((S)-2-(methylamino)propanamido)butanoyl)isoindoline-1-carboxamide hydrochloride | 0.040 | 9.264 |
| Example 31 | (S)-2-[(S)-3-Methyl-2-((S)-2-methylamino-propionylamino)-butyryl]-1,2,3,4-tetrahydro-isoquinoline-3-carboxylic acid (2,6-difluoro-phenyl)-amide | 0.037 | 13.44 |
| Example 32 | (S)-N-(2,6-difluorophenyl)-2-((2S,3S)-3-methoxy-2-((S)-2-(methylamino)propanamido)butanoyl)isoindoline-1-carboxamide hydrochloride | 0.024 | 51.74 |
| Example 33 | (S)-N-(2,6-difluorophenyl)-2-((2S,3R)-3-hydroxy-2-((S)-2-(methylamino)propanamido)butanoyl)isoindoline-1-carboxamide hydrochloride | 0.016 | >54.8 |
| Example 34 | (S)-N-(2,6-difluorophenyl)-2-((S)-2-((S)-2-(methylamino)propanamido)-2-phenylacetyl)isoindoline-1-carboxamide hydrochloride | 0.032 | |
| Example 35 | (S)-N-(2,6-difluorophenyl)-2-((S)-4-methyl-2-((S)-2-(methylamino)propanamido)pentanoyl)isoindoline-1-carboxamide hydrochloride | 0.027 | 33.67 |
| Example 36 | (S)-N-(2,6-dichlorophenyl)-2-((S)-3-methyl-2-((S)-2-(methylamino)propanamido)butanoyl)-1,2,3,4-tetrahydroisoquinoline-1-carboxamide hydrochloride | 0.025 | >54.8 |
| Example 37 | (S)-2-((S)-2-cyclopentyl-2-((S)-2-(methylamino)propanamido)acetyl)-N-(2,6-difluorophenyl)-1,2,3,4-tetrahydroisoquinoline-1-carboxamide hydrochloride | 0.034 | >54.8 |
| Example 38 | (S)-N-(2,6-difluorophenyl)-2-((S)-3,3-dimethyl-2-((S)-2-(methylamino)propanamido)butanoyl)-1,2,3,4-tetrahydroisoquinoline-1-carboxamide hydrochloride | 0.062 | >54.8 |
| Example 39 | (S)-N-(2,6-difluorophenyl)-2-((2S,3R)-3-methoxy-2-((S)-2-(methylamino)propanamido)butanoyl)-1,2,3,4-tetrahydroisoquinoline-1-carboxamide hydrochloride | 0.093 | >54.8 |
| Example 40 | (S)-N-(2,6-difluorophenyl)-2-((2S,3S)-2-((S)-2-(methylamino)propanamido)-3-phenylbutanoyl)isoindoline-1-carboxamide hydrochloride | 0.117 | >54.8 |

TABLE 8-continued

| Example | Name | BIR2 IC50 (μM) | BIR3 IC50 (μM) |
|---|---|---|---|
| Example 41 | N-(2,6-difluorophenyl)-7-fluoro-2-((S)-3-methyl-2-((S)-2-(methylamino)propanamido)butanoyl)-1,2,3,4-tetrahydroisoquinoline-1-carboxamide | 2.353 | >54.8 |
| Example 42 | N-(2,6-difluorophenyl)-7-fluoro-2-((S)-3-methyl-2-((S)-2-(methylamino)propanamido)butanoyl)-1,2,3,4-tetrahydroisoquinoline-1-carboxamide | 0.027 | >54.8 |
| Example 43 | N-(2,6-difluorophenyl)-6-fluoro-2-((S)-3-methyl-2-((S)-2-(methylamino)propanamido)butanoyl)-1,2,3,4-tetrahydroisoquinoline-1-carboxamide | 3.483 | >54.8 |
| Example 44 | 7-chloro-N-(2,6-difluorophenyl)-2-((S)-3-methyl-2-((S)-2-(methylamino)propanamido)butanoyl)-1,2,3,4-tetrahydroisoquinoline-1-carboxamide | 4.706 | >54.8 |
| Example 45 | 7-chloro-N-(2,6-difluorophenyl)-2-((S)-3-methyl-2-((S)-2-(methylamino)propanamido)butanoyl)-1,2,3,4-tetrahydroisoquinoline-1-carboxamide | 0.047 | >54.8 |
| Example 46 | 6-chloro-N-(2,6-difluorophenyl)-2-((S)-3-methyl-2-((S)-2-(methylamino)propanamido)butanoyl)-1,2,3,4-tetrahydroisoquinoline-1-carboxamide | 3.995 | >54.8 |
| Example 47 | (S)-N-(2-fluoro-6-methylphenyl)-2-((S)-3-methyl-2-((S)-2-(methylamino)propanamido)butanoyl)isoindoline-1-carboxamide hydrochloride | 0.019 | >54.8 |

The invention claimed is:

1. A compound of Formula I:

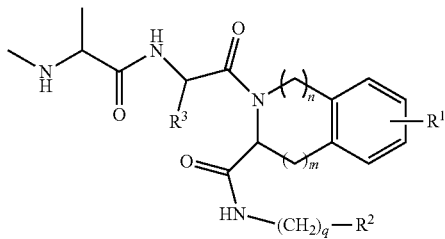

I wherein:
R$^1$ is halogen;
R$^2$ is selected from
aryl that optionally may be substituted with C$_{1-6}$-alkyl, OR$^4$, and halogen,
aryl that is fused with C$_{3-7}$-cycloalkyl, and
heteroaryl that optionally may be substituted with C$_{1-6}$-alkyl;
R$^3$ is selected from
C$_{1-6}$-alkyl that optionally may be substituted with OR$^4$ and aryl,
C$_{3-7}$-cycloalkyl,
heterocyclyl, and
aryl;
R$^4$ is selected from H and C$_{1-6}$-alkyl;
n is 1 or 2;
m is 0 or 1; and
q is 0, 1 or 2;
or a pharmaceutically acceptable salt thereof.

2. The compound according to claim 1 wherein R$^2$ is aryl that optionally may be substituted with OR$^4$, halogen and C$_{1-6}$-alkyl, or a pharmaceutically acceptable salt thereof.

3. The compound of claim 2 wherein R$^2$ is phenyl or naphthalenyl, or a pharmaceutically acceptable salt thereof.

4. The compound according to claim 1 wherein R$^2$ is heteroaryl that optionally may be substituted with C$_{1-6}$-alkyl, or a pharmaceutically acceptable salt thereof.

5. The compound of claim 4 wherein R$^2$ is selected from selected from quinolinyl, benzo[b]thiophenyl or indolyl.

6. The compound of claim 1 wherein R$^3$ is C$_{1-6}$-alkyl substituted with phenyl, or a pharmaceutically acceptable salt thereof.

7. The compound of claim 1 wherein R$^3$ is OR$^4$ and R$^4$ is H, or a pharmaceutically acceptable salt thereof.

8. The compound according to claim 1 wherein R$^3$ is C$_{3-7}$-cycloalkyl, or a pharmaceutically acceptable salt thereof.

9. The compound of claim 8 wherein R$^3$ is cyclohexyl or cyclopentyl, or a pharmaceutically acceptable salt thereof.

10. The compound according to claim 1 wherein R$^3$ is aryl, or a pharmaceutically acceptable salt thereof.

11. The compound of claim 10 wherein R$^3$ is phenyl.

12. The compound according to claim 1 wherein R$^3$ is heterocyclyl, or a pharmaceutically acceptable salt thereof.

13. The compound of claim 12 wherein R$^3$ is tetrahydropyran.

14. The compound according to claim 1 wherein m is o, n is 1, and q is o, or a pharmaceutically acceptable salt thereof.

15. The compound of claim 1 wherein R$^2$ is aryl, R$^3$ is C$_{1-6}$-alkyl, n is 1 and m and q are o.

16. The compound of claim 1, said compound being selected from the group consisting of:
(S)-2-[(S)-3-Methyl-2-((S)-2-methylamino-propionylamino)-butyryl]-2,3-dihydro-1H-isoindole-1-carboxylic acid (2,6-difluoro-phenyl)-amide hydrochloride;

((S)—N-(2, 6-dichlorophenyl)-2-((S)-3-methyl-2-((S)-2-(ethylamino)propanamido) butanoyl)isoindoline-1-carboxamide hydrochloride;
(S)—N-(2-chloro-6-fluorophenyl)-2-((S)-3-methyl-2-((S)-2-(methylamino) propanamido)butanoyl)isoindoline-1-carboxamide hydrochloride;
(S)—N-(benzo[b]thiophen-4-yl)-2-((S)-3-methyl-2-((S)-2-(methylamino)propanamido) butanoyl)isoindoline-1-carboxamide hydrochloride;
(S)—N-(2,6-difluorophenyl)-2-((2S,3S)-3-methyl-2-((S)-2-(methylamino) propanamido)pentanoyl)isoindoline-1-carboxamide hydrochloride;
(S)—N-(2,6-difluorophenyl)-2-((S)-3,3-dimethyl-2-((S)-2-(methylamino)propanamido) butanoyl)isoindoline-1-carboxamide hydrochloride;
2-((S)-3-methyl-2-((S)-2-(methylamino)propanamido) butanoyl)-N-phenylisoindoline-1-carboxamide hydrochloride;
N-(2-methoxyphenyl)-2-((S)-3-methyl-2-((S)-2-(methylamino)propanamido) butanoyl)isoindoline-1-carboxamide hydrochloride;
N-(2-methoxyphenyl)-2-((S)-3-methyl-2-((S)-2-(methylamino)propanamido) butanoyl)isoindoline-1-carboxamide hydrochloride;
N-benzyl-2-((S)-3-methyl-2-((S)-2-(methylamino)propanamido)butanoyl)isoindoline-1-carboxamide hydrochloride;
2-((S)-3-methyl-2-((S)-2-(methylamino)propanamido) butanoyl)-N-phenethylisoindoline-1-carboxamide hydrochloride;
(S)-2-((S)-3-methyl-2-((S)-2-(methylamino)propanamido)butanoyl)-N-(naphthalen-1-yl)isoindoline-1-carboxamide hydrochloride;
(R)-2-((S)-3-methyl-2-((S)-2-(methylamino)propanamido)butanoyl)-N-(naphthalen-1-yl)isoindoline-1-carboxamide hydrochloride;
(S)-2-((S)-3-methyl-2-((S)-2-(methylamino)propanamido)butanoyl)-N-(naphthalen-2-yl)isoindoline-1-carboxamide hydrochloride;
(S)—N-(2-fluorophenyl)-2-((S)-3-methyl-2-((S)-2-(methylamino)propanamido) butanoyl)isoindoline-1-carboxamide hydrochloride;
(S)—N-(2-chlorophenyl)-2-((S)-3-methyl-2-((S)-2-(methylamino)propanamido) butanoyl)isoindoline-1-carboxamide hydrochloride;
(S)-2-((S)-3-methyl-2-((S)-2-(methylamino)propanamido)butanoyl)-N-(5,6,7,8-tetrahydronaphthalen-1-yl)isoindoline-1-carboxamide hydrochloride;
(S)-2-((S)-3-methyl-2-((S)-2-(methylamino)propanamido)butanoyl)-N-(quinolin-8-yl)isoindoline-1-carboxamide hydrochloride;
N-(isoquinolin-1-yl)-2-((S)-3-methyl-2-((S)-2-(methylamino)propanamido) butanoyl)isoindoline-1-carboxamide hydrochloride;
(S)—N-(1-methyl-1H-indol-4-yl)-2-((S)-3-methyl-2-((S)-2-(methylamino)propanamido) butanoyl)isoindoline-1-carboxamide hydrochloride;
(S)—N-(2,6-difluorophenyl)-2-((2S,3S)-3-methoxy-2-((S)-2-(methylamino) propanamido)butanoyl)isoindoline-1-carboxamide hydrochloride;
(S)—N-(2,6-difluorophenyl)-2-((2S,3R)-3-hydroxy-2-((S)-2-(methylamino) propanamido)butanoyl)isoindoline-1-carboxamide hydrochloride;
(S)—N-(2,6-difluorophenyl)-2-((S)-4-methyl-2-((S)-2-(methylamino)propanamido)pentanoyl)isoindoline-1-carboxamide hydrochloride;
(S)—N-(2,6-difluorophenyl)-2-((2S,3S)-2-((S)-2-(methylamino)propanamido)-3-phenylbutanoyl)isoindoline-1-carboxamide hydrochloride; and
(S)—N-(2-fluoro-6-methylphenyl)-2-((S)-3-methyl-2-((S)-2-(methylamino) propanamido)butanoyl)isoindoline-1-carboxamide hydrochloride;
or a pharmaceutically acceptable salt of any of the foregoing compounds.

17. The compound of claim 1, said compound being selected from the group consisting of:
(S)-2-[(S)-3-Methyl-2-((S)-2-methylamino-propionylamino)-butyryl]-1,2,3,4-tetrahydro-isoquinoline-1-carboxylic acid (2-chloro-6-fluoro-phenyl)-amide hydrochloride;
6-Chloro-2-[(S)-3-methyl-2-((S)-2-methylamino-propionylamino)-butyryl]-1,2,3,4-tetrahydro-isoquinoline-1-carboxylic acid (2,6-difluoro-phenyl)-amide;
6-Fluoro-2-[(S)-3-methyl-2-((S)-2-methylamino-propionylamino)-butyryl]-1,2,3,4-tetrahydro-isoquinoline-1-carboxylic acid (2,6-difluoro-phenyl)-amide;
(S)—N-(2, 6-difluorophenyl)-2-((2S,3S)-3-methyl-2-((S)-2-(methylamino) propanamido)pentanoyl)-1,2,3,4-tetrahydroisoquinoline-1-carboxamide hydrochloride;
(S)—N-(2,6-difluorophenyl)-2-((S)-3-methyl-2-((S)-2-(methylamino) propanamido)butanoyl)-1,2,3,4-tetrahydroisoquinoline-1-carboxamide hydrochloride;
(S)—N-(2, 6-dichlorophenyl)-2-((S)-3-methyl-2-((S)-2-(methylamino)propanamido) butanoyl)-1,2,3,4-tetrahydroisoquinoline-1-carboxamide hydrochloride;
(S)—N-(2,6-difluorophenyl)-2-((S)-3,3-dimethyl-2-((S)-2-(methylamino)propanamido) butanoyl)-1,2,3,4-tetrahydroisoquinoline-1-carboxamide hydrochloride;
(S)—N-(2,6-difluorophenyl)-2-((2S,3R)-3-methoxy-2-((S)-2-(methylamino) propanamido)butanoyl)-1,2,3,4-tetrahydroisoquinoline-1-carboxamide hydrochloride;
N-(2,6-difluorophenyl)-7-fluoro-2-((S)-3-methyl-2-((S)-2-(methylamino) propanamido)butanoyl)-1,2,3,4-tetrahydroisoquinoline-1-carboxamide;
N-(2,6-difluorophenyl)-7-fluoro-2-((S)-3-methyl-2-((S)-2-(methylamino) propanamido)butanoyl)-1,2,3,4-tetrahydroisoquinoline-1-carboxamide;
N-(2,6-difluorophenyl)-6-fluoro-2-((S)-3-methyl-2-((S)-2-(methylamino) propanamido)butanoyl)-1,2,3,4-tetrahydroisoquinoline-1-carboxamide;
7-chloro-N-(2,6-difluorophenyl)-2-((S)-3-methyl-2-((S)-2-(methylamino) propanamido)butanoyl)-1,2,3,4-tetrahydroisoquinoline-1-carboxamide;
7-chloro-N-(2,6-difluorophenyl)-2-((S)-3-methyl-2-((S)-2-(methylamino) propanamido)butanoyl)-1,2,3,4-tetrahydroisoquinoline-1-carboxamide; and
6-chloro-N-(2,6-difluorophenyl)-2-((S)-3-methyl-2-((S)-2-(methylamino) propanamido)butanoyl)-1,2,3,4-tetrahydroisoquinoline-1-carboxamide;
or a pharmaceutically acceptable salt of any of the foregoing compounds.

18. The compound of claim 1, said compound being (S)—N-(2,6-difluorophenyl)-2-((S)-3-methyl-2-((S)-2-(methylamino)propanamido) butanoyl)-1, 2,3,4-tetrahydroisoquinoline-3-carboxamide;
or a pharmaceutically acceptable salt thereof.

19. The compound of claim 1, said compound being selected from the group consisting of:
(S)-2-[(S)-2-Cyclohexyl-2-((S)-2-methylamino-propionylamino)-acetyl]-2,3-dihydro-1H-isoindole-1-carboxylic acid (2,6-difluoro-phenyl)-amide hydrochloride; and (S)-2-((S)-2-cyclopentyl-2-((S)-2-(methylamino)propanamido)acetyl)-N-(2,6-difluorophenyl)isoindoline-1-carboxamide hydrochloride;

or a pharmaceutically acceptable salt of either of the foregoing compounds.

20. The compound of claim 1, said compound being selected from the group consisting of:

(S)-2-[(S)-2-Cyclohexyl-2-((S)-2-methylamino-propionylamino)-acetyl]-1,2,3,4-tetrahydro-isoquinoline-1-carboxylic acid (2,6-difluoro-phenyl)-amide hydrochloride; and (S)-2-((S)-2-cyclopentyl-2-((S)-2-(methylamino)propanamido)acetyl)-N-(2,6-difluorophenyl)-1,2,3,4-tetrahydroisoquinoline-1-carboxamide hydrochloride;

or a pharmaceutically acceptable salt of either of the foregoing compounds.

21. The compound of claim 1, said compound being selected from the group consisting of:

(S)—N-(2,6-difluorophenyl)-2-((S)-2-((S)-2-(methylamino)propanamido)-2-(tetrahydro-2H-pyran-4-yl)acetyl)isoindoline-1-carboxamide hydrochloride; and (S)—N-(2,6-difluorophenyl)-2-((S)-2-((S)-2-(methylamino)propanamido)-2-(tetrahydro-2H-pyran-4-yl)acetyl)-1,2,3,4-tetrahydroisoquinoline-1-carboxamide hydrochloride;

or a pharmaceutically acceptable salt of either of the foregoing compounds.

22. The compound of claim 1, said compound being (S)—N-(2,6-difluorophenyl)-2-((S)-2-((S)-2-(methylamino)propanamido)-2-phenylacetyl)isoindoline-1-carboxamide hydrochloride;

or a pharmaceutically acceptable salt of the foregoing compound.

23. The compound according to claim 1, selected from the group consisting of:

(S)-2-[(S)-3-Methyl-2-((S)-2-methylamino-propionylamino)-butyryl]-2,3-dihydro-1H-isoindole-1-carboxylic acid (2,6-difluoro-phenyl)-amide hydrochloride;

((S)-2-[(S)-2-Cyclohexyl-2-((S)-2-methylamino-propionylamino)-acetyl]-2,3-dihydro-1H-isoindole-1-carboxylic acid (2,6-difluoro-phenyl)-amide hydrochloride;

(S)—N-(2, 6-difluorophenyl)-2-((S)-3-methyl-2-((S)-2-(methylamino) propanamido)butanoyl)isoindoline-1-carboxamide hydrochloride;

(S)-2-[(S)-3-Methyl-2-((S)-2-methylamino-propionylamino)-butyryl]-1,2,3,4-tetrahydro-isoquinoline-1-carboxylic acid (2-chloro-6-fluoro-phenyl)-amide hydrochloride;

6-Chloro-2-[(S)-3-methyl-2-((S)-2-methylamino-propionylamino)-butyryl]-1,2,3,4-tetrahydro-isoquinoline-1-carboxylic acid (2,6-difluoro-phenyl)-amide;

6-Fluoro-2-[(S)-3-methyl-2-((S)-2-methylamino-propionylamino)-butyryl]-1,2,3,4-tetrahydro-isoquinoline-1-carboxylic acid (2,6-difluoro-phenyl)-amide;

(S)—N-(2,6-dichlorophenyl)-2-((S)-3-methyl-2-((S)-2-(methylamino)propanamido) butanoyl)isoindoline-1-carboxamide hydrochloride;

(S)—N-(2-chloro-6-fluorophenyl)-2-((S)-3-methyl-2-((S)-2-(methylamino) propanamido)butanoyl)isoindoline-1-carboxamide hydrochloride;

(S)—N-(benzo[b]thiophen-4-yl)-2-((S)-3-methyl-2-((S)-2-(methylamino) propanamido)butanoyl)isoindoline-1-carboxamide hydrochloride;

(S)—N-(2,6-difluorophenyl)-2-((2S,3S)-3-methyl-2-((S)-2-(methylamino) propanamido)pentanoyl)isoindoline-1-carboxamide hydrochloride;

(S)—N-(2,6-difluorophenyl)-2-((S)-3,3-dimethyl-2-((S)-2-(methylamino) propanamido)butanoyl)isoindoline-1-carboxamide hydrochloride;

(S)—N-(2, 6-difluorophenyl)-2-((S)-2-((S)-2-(methylamino)propanamido)-2-(tetrahydro-2H-pyran-4-yl) acetyl)isoindoline-1-carboxamide hydrochloride;

(S)-2-((S)-2-cyclopentyl-2-((S)-2-(methylamino)propanamido)acetyl)-N-(2,6-difluorophenyl)isoindoline-1-carboxamide hydrochloride;

(S)—N-(2,6-difluorophenyl)-2-((S)-2-((S)-2-(methylamino)propanamido)-2-(tetrahydro-2H-pyran-4-yl)acetyl)-1,2,3,4-tetrahydroisoquinoline-1-carboxamide hydrochloride;

(S)—N-(2,6-difluorophenyl)-2-((2S,3S)-3-methyl-2-((S)-2-(methylamino) propanamido)pentanoyl)-1,2,3,4-tetrahydroisoquinoline-1-carboxamide hydrochloride; and N-(2,6-difluorophenyl)-7-fluoro-2-((S)-3-methyl-2-((S)-2-(methylamino) propanamido)butanoyl)-1,2,3,4-tetrahydroisoquinoline-1-carboxamide;

or a pharmaceutically acceptable salt of each of the foregoing compounds.

* * * * *